United States Patent
Sato et al.

(10) Patent No.: US 11,407,980 B2
(45) Date of Patent: Aug. 9, 2022

(54) CELL CULTURE MEDIUM FOR CULTURING ORGANOID, CULTURE METHOD, AND ORGANOID

(71) Applicant: KEIO UNIVERSITY, Tokyo (JP)

(72) Inventors: Toshiro Sato, Tokyo (JP); Mami Matano, Tokyo (JP)

(73) Assignee: KEIO UNIVERSITY, Tokyo (JP)

( * ) Notice: Subject to any disclaimer, the term of this patent is extended or adjusted under 35 U.S.C. 154(b) by 880 days.

(21) Appl. No.: 16/301,717

(22) PCT Filed: May 10, 2017

(86) PCT No.: PCT/JP2017/017681
§ 371 (c)(1),
(2) Date: Sep. 11, 2019

(87) PCT Pub. No.: WO2017/199811
PCT Pub. Date: Nov. 23, 2017

(65) Prior Publication Data
US 2019/0390171 A1    Dec. 26, 2019

(30) Foreign Application Priority Data
May 18, 2016   (JP) .............................. JP2016-099995

(51) Int. Cl.
*C12N 5/09*   (2010.01)
(52) U.S. Cl.
CPC ........ *C12N 5/0693* (2013.01); *C12N 2500/90* (2013.01); *C12N 2501/105* (2013.01); *C12N 2501/115* (2013.01); *C12N 2501/415* (2013.01); *C12N 2501/998* (2013.01)
(58) Field of Classification Search
CPC ............. C12N 5/0693; C12N 2500/90; C12N 2501/105; C12N 2501/115; C12N 2501/415
See application file for complete search history.

(56) References Cited

U.S. PATENT DOCUMENTS

| | | | |
|---|---|---|---|
| 5,905,041 A | 5/1999 | Beug et al. | |
| 2006/0148694 A1 | 7/2006 | Ullrich et al. | |
| 2010/0216181 A1 | 8/2010 | Daigh et al. | |
| 2010/0279403 A1 | 11/2010 | Rajesh et al. | |
| 2012/0028355 A1 | 2/2012 | Sato et al. | |
| 2013/0164787 A1 | 6/2013 | Agulnick et al. | |
| 2014/0243227 A1 | 8/2014 | Clevers et al. | |
| 2016/0101133 A1 | 4/2016 | Basu et al. | |
| 2017/0044489 A1 | 2/2017 | Barry et al. | |
| 2017/0275593 A1* | 9/2017 | Hanna .................. | C12N 5/0606 |

FOREIGN PATENT DOCUMENTS

| | | |
|---|---|---|
| CN | 104024401 A | 9/2014 |
| JP | H09-502359 A | 3/1997 |
| JP | 2008-523787 A | 7/2008 |
| JP | 2011-84580 A | 4/2011 |
| JP | 2012-518415 A | 8/2012 |
| JP | 2012-519005 A | 8/2012 |
| JP | 5458112 B2 | 4/2014 |
| JP | 2014-516562 A | 7/2014 |
| JP | 2016-506736 A | 3/2016 |
| WO | 2006/063415 A1 | 6/2006 |
| WO | 2014/124172 A1 | 8/2014 |
| WO | 2014182885 A2 | 11/2014 |
| WO | 2015121471 A1 | 8/2015 |
| WO | 2015/196012 A1 | 12/2015 |

OTHER PUBLICATIONS

Date, S., and Sato, T., Mini-gut organoids: reconstituteion of the stem cell niche. Annual Review of Cell and Development Biology, vol. 31 (2015) pp. 269-289. (Year: 2015).*
International Search Report dated Jun. 6, 2017 during the prosecution of International Patent Application No. PCT/JP2017/017681.
Chinese First Office Action issued in corresponding Chinese Patent Application No. 2017800380549 dated Jun. 7, 2021 with translation, 15 pages total.
Date, Shoichi and Sato, Toshiro, "Mini-Gut Organoids: Reconstitution of the Stem Cell Niche," Annu. Rev. Cell Dev. Biol. (2015) vol. 31, pp. 31.1-32.21.
Hubert, Christopher G. et al., "A three-dimensional organoid culture system derived from human glioblastomas recapitulates the hypoxic gradients and cancer stem cell heterogeneity of tumors found in vivo," Cancer Res. (2016) vol. 78, Issue 8, pp. 2465-2477.
Mihara, Emiko et al., "Active and water-soluble form of lapidated Wnt protein is maintained by a serum glycoprotein afamin/a-albumin," eLife (2016) vol. 5, ell621, 19 pages total.
Sato, Toshiro et al., "Long-term Expansion of Epithelial Organoids From Human Colon, Adenoma, Adenocarcinoma, and Barrett's Epithelium," GASTROENTEROLOGY (2011) vol. 141, No. 5, pp. 1762-1772.
International Preliminary Report on Patentability issued in corresponding International Patent Application No. PCT/JP2017/017681 dated Feb. 13, 2018, with English translation.
Tanaka, 178(11):820-821, Journal of Clinical and Experimental Medicine (Sep. 14, 1996)—document in Japanese cited in IPRP issued in Appln. No. PCT/JP2017/017681 dated Feb. 13, 2018 as document 9.

(Continued)

*Primary Examiner* — Kara D Johnson
(74) *Attorney, Agent, or Firm* — Troutman Pepper Hamilton Sanders LLP

(57) ABSTRACT

A cell culture medium for culturing organoid containing at least two types of components selected from the group consisting of insulin-like growth factor 1 (IGF1), fibroblast growth factor 2 (FGF2) and epiregulin (EREG), and at least one type of component among the following components i) to iii): i) Wnt agonist, ii) bone morphogenetic protein (BMP) inhibitor, and iii) transforming growth factor-β (TGF-β) inhibitor.

12 Claims, 7 Drawing Sheets

(56) References Cited

OTHER PUBLICATIONS

Shioi, T., "Role of phosphoinositide 3-kinase pathway in cardiac hypertrophy", 207(7):456-462, Journal of Clinical and Experimental Medicine (May 18, 2002)—document in Japanese cited in IPRP issued in Appln. No. PCT/JP2017/017681 dated Feb. 13, 2018 as document 8.

Extended European Search Report issued in corresponding European Patent Application No. 20 16 4158 dated May 13, 2020.

* cited by examiner

FIG. 7

|  | ENAS | IFNA |
|---|---|---|
| WR− | ○ | ◎ |
| WR+ | ○ | ◎ |
| WR$^{Afm}$+ | ◎ | ◎◎ |

※RESPECTIVELY CULTURED UNDER NORMOXIA AND HYPOXIA CONDITIONS

CELL CULTURE MEDIUM FOR CULTURING ORGANOID, CULTURE METHOD, AND ORGANOID

CROSS REFERENCE TO RELATED APPLICATIONS

This is a U.S. National Phase Application under 35 U.S.C. § 371 of International Patent Application No. PCT/JP2017/017681, filed May 10, 2017, which claims priority of Japanese Patent Application No. 2016-099995, filed May 18, 2016. The entire contents of which are hereby incorporated by reference.

FIELD OF THE INVENTION

The present invention relates to a cell culture medium for culturing an organoid, a culture method and an organoid.

BACKGROUND

The intestinal tract is the organ that has the largest surface area in contact with the outside world in the body, and has functions that are indispensable for maintaining life such as digestion and absorption. The majority of intestinal tract functions are fulfilled by intestinal epithelium that covers the inner layer thereof. Intestinal epithelium is composed of two components consisting of cilia comprised of three types of differentiated cells (mucus-producing cells, absorptive epithelial cells and endocrine cells) and crypts mainly comprised of undifferentiated germ cells. Paneth cells that produce antimicrobial peptides are present at the base of crypts of the small intestine. Recently, Lgr5-positive cells (also referred to as crypt base columnar (CBC) cells) have been determined by molecular genetics-based cell lineage analysis to be intestinal epithelial stem cells. Although Lgr5-positive intestinal epithelial stem cells produce progenitor cells referred to as transit amplifying cells, these progenitor cells do not have a permanent self-replicating ability, but rather differentiation ability is limited to one to three cell lines. Transit amplifying cells differentiate together with two to four cycles of cell division in crypts and achieve terminal differentiation in cilia. These differentiated cells detach at the tips of cilia and die due to apoptosis. Intestinal epithelium is tissue that has a fast metabolism and migrates from crypt stem cells to the tips of cilia in four to five days. Differing from other differentiated cells, Paneth cells migrate to the bottoms of crypts accompanying differentiation and have a long cell life of two months.

The self-replication mechanism of intestinal epithelial stem cells is known to be controlled by a Wnt signal and bone morphogenetic protein (BMP) signal based on results in several genetically modified mice. Knockout mice specific for intestinal epithelium expressing Wnt signal inhibitory molecules in the form of adenomatous polyposis coli (APC) exhibit hyperproliferation and adenoma formation. In addition, ectopic crypt formation has been observed in mice demonstrating overexpression of BMP inhibitory protein in the form noggin in intestinal epithelial cells, suggesting that the BMP signal acts to inhibit intestinal epithelial stem cells. In actuality, the Wnt signal is highly active at the bases of crypts and a gradient has been observed by which that activity becomes lower towards the lumen. On the other hand, the BMP signal is known to exhibit a gradient opposite that from the Wnt signal.

In addition, long-term culturing of intestinal epithelial cells has long been impossible. This is thought to be due to the growth factors required for maintaining intestinal epithelial stem cells being unknown. In recent years, long-term maintenance of intestinal epithelial stem cells has been successful by adhering intestinal epithelial stem cells to extracellular matrix and culturing in the presence of cell culture medium containing basal medium for animal or human cells to which has been added BMP inhibitor, mitogenic growth factor and Wnt agonist (see, for example, Japanese Patent No. 5458112).

SUMMARY

Problems to be Solved by the Invention

The cell culture media used in the culture method described in Japanese Patent No. 5458112 had the problem of a decrease in expression of epidermal growth factor receptor (EGFR) caused by stimulation of epidermal growth factor (EGF). In contrast, the addition of p38 inhibitor made it possible to maintain expression of EGFR. However, media and culture methods incorporating p38 inhibitor may cause inhibition of differentiation or cell death, thereby preventing culturing of some human tissue and tumor tissue.

In order to solve the aforementioned problems, the present invention provides a cell culture medium for culturing organoid enabling long-term culturing of epithelial stem cells, epithelial cells or epithelial tumor cells derived from mammals, including humans, tissue at least containing any one of these cells, or tissue unable to be cultured in the prior art.

In addition, the present invention provides a cultured human organoid able to be produced in the absence of serum. In addition, the present invention provides a cultured human organoid produced from tissue in which the production thereof was previously not possible.

As a result of conducting extensive studies to solve the aforementioned problems, the inventors of the present invention discovered the composition of a cell culture medium for culturing organoid that enables long-term culturing of epithelial stem cells, epithelial cells or epithelial tumor cells derived from mammals, including humans, tissue at least containing any one of these cells, or tissue unable to be cultured in the prior art. In addition, the inventors of the present invention found that an organoid can be formed by culturing epithelial stem cells, epithelial cells or epithelial tumor cells derived from mammals, including humans, tissue at least containing any one of these cells, or tissue unable to be cultured in the prior art, under hypoxic condition.

Namely, the present invention includes the aspects indicated below.

The cell culture medium for culturing organoid according to a first aspect of the present invention contains at least two types of components selected from the group consisting of insulin-like growth factor 1 (IGF1), fibroblast growth factor 2 (FGF2) and epiregulin (EREG), and at least one type of component among the following components i) to iii):
  i) Wnt agonist,
  ii) bone morphogenetic protein (BMP) inhibitor, and
  iii) transforming growth factor-β (TGF-β) inhibitor.

The cell culture medium for culturing organoid according to the aforementioned first aspect may substantially not contain EGF and p38 inhibitor.

The cell culture method for culturing organoid according to the aforementioned first aspect may also contain IGF1 and FGF2.

The Wnt agonist may be at least one type selected from the group consisting of Wnt protein, R-spondin and GSK-3β inhibitor.

The Wnt protein may form a complex with afamin, which is a stabilizing substance thereof.

The Wnt agonist may be Wnt protein and R-spondin.

The cell culture medium for culturing organoid described in any one of claims 4 to 6, wherein the Wnt protein is at least one type selected from the group consisting of Wnt1, Wnt2, Wnt2b, Wnt3, Wnt3a, Wnt4, Wnt5a, Wnt5b, Wnt6, Wnt7a, Wnt7b, Wnt8a, Wnt8b, Wnt9a, Wnt9b, Wnt10a, Wnt10b, Wnt11 and Wnt16.

The R-spondin may be at least one type selected from the group consisting of R-spondin 1, R-spondin 2, R-spondin 3 and R-spondin 4.

The BMP inhibitor may be at least one type selected from the group consisting of noggin, gremlin, chordin, chordin-like protein containing a chordin domain, follistatin, follistatin-related protein containing a follistatin domain, DAN, DAN-like protein containing a DAN cysteine knot domain, sclerostin/SOST and α-2 macroglobulin.

The BMP inhibitor may be noggin.

The TGF-β inhibitor may be at least one type selected from the group consisting of A83-01, SB-431542, SB-505124, SB-525334, SD-208, LY-36494 and SJN-2511.

The TGF-β inhibitor may be A83-01.

The culture method according to a second aspect of the present invention is a method for culturing epithelial stem cells, epithelial cells, epithelial tumor cells or tissue at least containing any one of these cells; provided with: an extracellular matrix preparation step for preparing an extracellular matrix, an adhesion step for adhering epithelial stem cells, epithelial cells, epithelial tumor cells or tissue at least containing any one of these cells onto the extracellular matrix, and an organoid formation step for forming an organoid by adding the cell culture medium for culturing organoid according to the aforementioned first aspect and culturing the epithelial stem cells, the epithelial cells, the epithelial tumor cells or tissue at least containing any one of these cells, after the cell adhesion step.

In the organoid formation step, an organoid may be formed by culturing the epithelial stem cells, the epithelial cells, the epithelial tumor cells or tissue at least containing any one of these cells under hypoxic condition at an oxygen concentration of 15% to 0.1%.

The organoid containing differentiated cells according to a third aspect of the present invention is obtained by the method according to the aforementioned second aspect.

The organoid containing cells differentiated cells according to the aforementioned third aspect may be for regenerative medicine.

The culture method according to a fourth aspect of the present invention is a method for culturing the epithelial stem cells, the epithelial cells, the epithelial tumor cells or tissue at least containing any one of these cells; provided with: an extracellular matrix preparation step for preparing an extracellular matrix, an adhesion step for adhering epithelial stem cells, epithelial cells, epithelial tumor cells or tissue at least containing any one of these cells onto the extracellular matrix, and an organoid formation step for forming an organoid by adding the cell culture medium for culturing organoid and culturing the epithelial stem cells, the epithelial cells, the epithelial tumor cells or tissue at least containing any one of these cells under hypoxic condition at an oxygen concentration of 15% to 0.1%, after the cell adhesion step; wherein, the cell culture medium for culturing organoid contains at least one type selected from the group consisting of Wnt agonist, mitogenic growth factor, BMP inhibitor, TGF-β inhibitor and p38 inhibitor.

The Wnt agonist may be at least one type selected from the group consisting of Wnt protein, R-spondin and GSK-3β inhibitor.

The Wnt protein may form a complex with afamin, which is a stabilizing substance thereof.

The Wnt agonist may be Wnt protein and R-spondin.

The Wnt protein may be at least one type selected from the group consisting of Wnt1, Wnt2, Wnt2b, Wnt3, Wnt3a, Wnt4, Wnt5a, Wnt5b, Wnt6, Wnt7a, Wnt7b, Wnt8a, Wnt8b, Wnt9a, Wnt9b, Wnt10a, Wnt10b, Wnt11 and Wnt16.

The R-spondin may be at least one type selected from the group consisting of R-spondin 1, R-spondin 2, R-spondin 3 and R-spondin 4.

The BMP inhibitor may be at least one type selected from the group consisting of noggin, gremlin, chordin, chordin-like protein containing a chordin domain, follistatin, follistatin-related protein containing a follistatin domain, DAN, DAN-like protein containing a DAN cysteine knot domain, sclerostin/SOST and α-2 macroglobulin.

The BMP inhibitor may be noggin.

The TGF-β inhibitor may be at least one type selected from the group consisting of A83-01, SB-431542, SB-505124, SB-525334, SD-208, LY-36494 and SJN-2511.

The TGF-β inhibitor may be A83-01.

The organoid containing differentiated cells according to a fifth aspect of the present invention is obtained by the culture method according to the aforementioned fourth aspect.

The organic containing differentiated cells according to the aforementioned fifth aspect may be for regenerative medicine.

According to the cell culture method for culturing organoid of the aforementioned aspects, epithelial stem cells, epithelial cells or epithelial tumor cells derived from mammals, including humans, tissue at least containing any one of these cells, or tissue unable to be cultured in the prior art, can be cultured for a long period of time. In addition, an organoid can be formed with high efficiency from at least any one of the aforementioned cells and aforementioned tissue.

BRIEF DESCRIPTION OF THE DRAWINGS

FIG. 7 is a table indicating the results of having evaluated organoid formation efficiency in cell culture medium for culturing organoid of the present embodiment having different compositions.

DETAILED DESCRIPTION

<<Cell Culture Medium for Culturing Organoid>>

Figure 1:
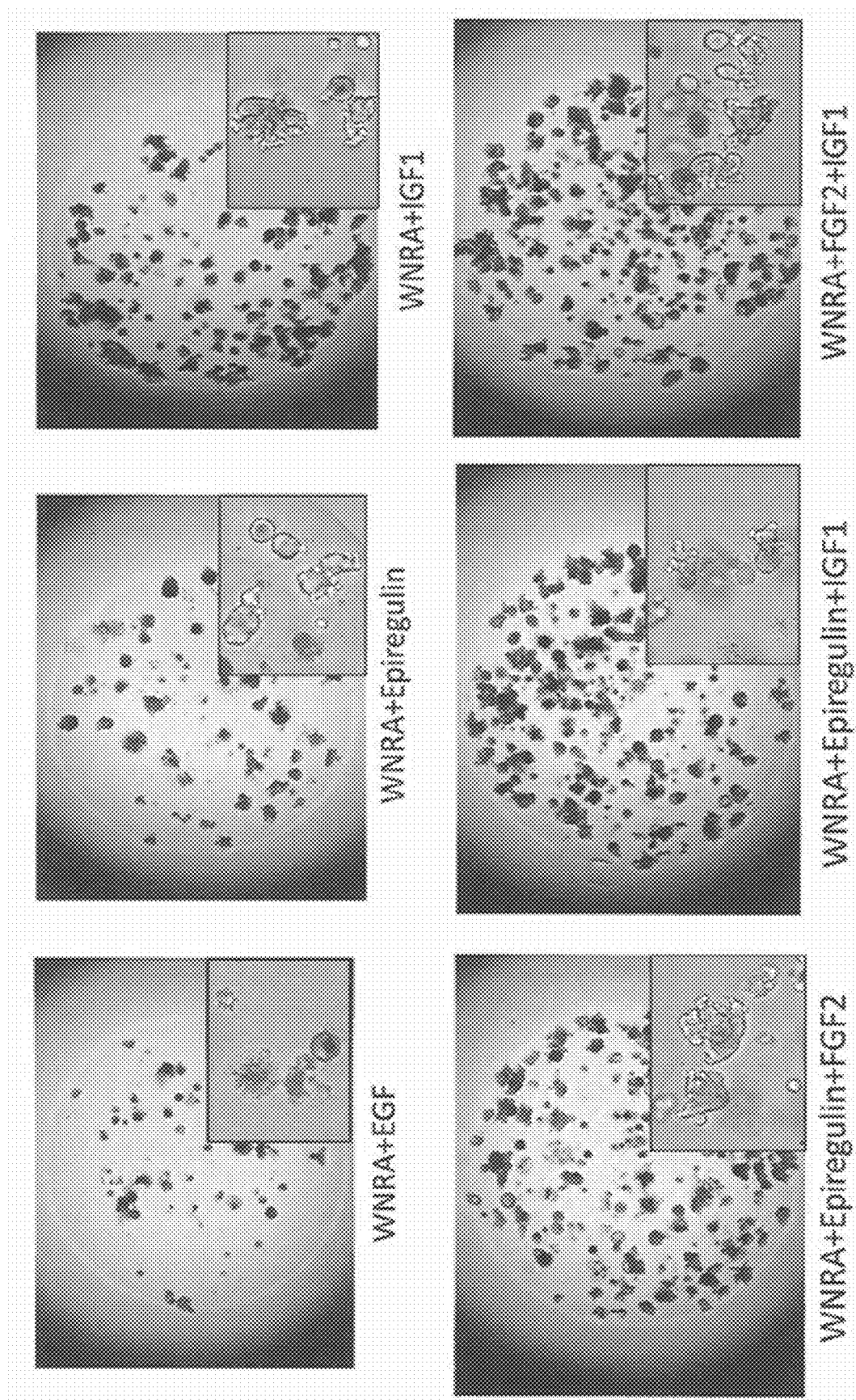
FIG. 1 depicts images showing cultured organoids of human epithelial tumor cells on day 7 from the start of primary culturing (passage 0) in each of the media of Example 1. Here, W represents Wn-3A, N represents noggin, R represents R-spondin 1 and A represents A83-01.

The cell culture medium for culturing organoid according a first embodiment of the present invention contains at least two types of components selected from the group consisting of IGF1, FGF2 and EREG and at least one type of component among the following components i) to iii):
 i) Wnt agonist,
 ii) bone morphogenetic protein (BMP) inhibitor, and
 iii) transforming growth factor-β (TGF-β) inhibitor.

According to the cell culture medium for culturing organoid of the present embodiment, tissue can be cultured over a long period of time that does not substantially contain EGF or p38 inhibitor but contains epithelial stem cells, epithelial cells or epithelial tumor cells derived from mammals, including humans, or tissue at least containing any one of these cells, or tissue unable to be cultured in the prior art.

In addition, according to the cell culture medium for culturing organoid of the present embodiment, an organoid can be formed with high efficiency from epithelial stem cells, epithelial cells or epithelial tumor cells derived from mammals, including humans, tissue at least containing any one of these cells, or tissue unable to be cultured in the prior art.

In addition, the differentiation ability of epithelial stem cells cultured using the cell culture medium for culturing organoid of the present embodiment can be maintained over a long period of time and the tumor incidence thereof is extremely low.

In the present description, epithelial cells include differentiated epithelial cells and epithelial stem cells acquired from epithelial tissue. "Epithelial stem cells" refers to stem cells derived from epithelial tissue that have the ability to self-replicate and differentiate into differentiated epithelial cells for a long period of time. Examples of epithelial tissue include the cornea, oral mucosa, skin, conjunctiva, bladder, uriniferous tubules, kidneys, digestive organs (esophagus, stomach, duodenum, small intestine (including the jejunum and ileum) and large intestine (including the colon)), liver, pancreas, mammary glands, saliva glands, lacrimal glands, prostate gland, hair roots, trachea and lungs. Among these, the cell culture medium for culturing organoid of the present embodiment is particularly preferably used to culture epithelial cells derived from digestive organs (esophagus, stomach, duodenum, small intestine (including the jejunum and ileum) and large intestine (including the colon)), liver and pancreas.

In addition, in the present description, "epithelial tumor cells" refer to the aforementioned cells derived from epithelial tissue that have become tumorigenic.

In the present description, an "organoid" refers to a three-dimensional cellular organ that is self-organized by accumulating cells at high density in a controlled space.

In the present description, "substantially not containing" refers to not containing a specific component at all or only containing a specific component at a concentration at which the function thereof is not demonstrated.

Accordingly, "substantially not containing EGF or p38 inhibitor" refers to not containing EGF or p38 inhibitor at all or only containing EGF and p38 inhibitor at a concentration at which inhibition of the expression of EGFR by EGF and inhibition of differentiation and cell death caused by p38 inhibitor do not occur.

The cell culture medium for culturing organoid of the present embodiment at least contains one type of factor selected from the group consisting of IGF1, FGF2 and epiregulin, and whether any one of the aforementioned three types of factors are contained can be suitably selected corresponding to the type of cells or tissue cultured. Among these, the cell culture medium for culturing organoid of the present embodiment preferably contains IGF1 and epiregulin, FGF2 and epiregulin or IGF1 and FGF2 and more preferably contains IGF1 and FGF2. As a result of containing the aforementioned factors, epithelial stem cells, epithelial cells or epithelial tumor cells derived from mammals, including humans, tissue at least containing these cells, or tissue unable to be cultured in the prior art, can be cultured for a long period of time without substantially containing EGF and p38 inhibitor. In addition, an organoid can be formed with high efficiency from epithelial stem cells, epithelial cells or epithelial tumor derived from mammals, including humans, tissue at least containing any one of these cells, or tissue unable to be cultured in the prior art.

The following provides a detailed explanation of constituents of the cell culture medium for culturing organoid of the present embodiment.

<Cell Culture Basal Medium>

All types of serum-free cell culture basal media are included in the cell culture medium for culturing organoid of the present embodiment. The cell culture medium for culturing organoid of the present embodiment is preferably for animal cells or human cells.

Examples of this serum-free cell culture basal media include prescribed synthetic media buffered with a carbonic acid-based buffering solution to pH 7.2 to pH 7.6. More specifically, examples include glutamine, insulin, B27 supplement (Thermo Fisher), N-acetyl-L-cysteine (Wako Pure Chemical Industries), penicillin or streptomycin and Dulbecco's modified Eagle medium/Ham's F-12 mixed medium supplemented with transferrin (Dulbecco's Modified Eagle Medium: Nutrient Mixture F-12 (DMEM/F12)).

In addition, other examples include Roswell Park Memorial Instituted (RPMI) 1640 medium, DMEM/F12 and Advanced RPMI medium instead of advanced Dulbecco's modified Eagle medium/Ham's F-12 mixed medium.

The aforementioned cell culture medium for culturing organoid of the present embodiment does not substantially contain indeterminate components such as fetal bovine serum (FBS) or fetal calf serum.

In addition, the aforementioned cell culture medium for culturing organoid may contain 5% serum.

<Wnt Agonist>

In the present description, a "Wnt agonist" refers to a chemical agent that activates T-cell factor (TCF)/lymphoid enhancer factor (LEF)-mediated transcription in cells. Accordingly, Wnt agonists are not limited to Wnt family proteins, but also include Wnt agonists that activated by bonding to members of the frizzled receptor family, intracellular β-catenin destruction inhibitors and TCF/LEF activating substances. The Wnt agonist is preferably at least one type selected from the group consisting of Wnt protein, R-spondin and GSK-3β inhibitor.

The Wnt agonist stimulates Wnt activity in cells by at least 10%, preferably at least 20%, more preferably at least 30%, even more preferably at least 50% and particularly preferably at least 90% in comparison with the level of Wnt activity in the absence of the Wnt agonist. Wnt activity can be investigated using a method known by persons with ordinary skill in the art such as by measuring Wnt transcription activity with pTOPFLASH and pFOPFLASH Tcf luciferase reporter constructs (reference document: Korinek, et al., 1997, Science 275: 1784-1787).

The Wnt agonist is preferably contained when culturing epithelial stem cells, epithelial cells, epithelial tumor cells or tissue at least containing any one of these cells. The Wnt agonist contained in the cell culture medium for culturing organoid of the present embodiment more preferably includes a complex of Wnt protein and afamin and even more preferably contains both a complex of Wnt protein and afamin, and R-spondin. Epithelial stem cells or epithelial cells are able form organoids with high efficiency as a result of the cell culture medium for culturing organoid of the present embodiment containing a complex of Wnt protein and afamin, and R-spondin.

[Wnt Protein]

There are no particular limitations on the origin of the Wnt protein serving as a type of Wnt agonist and Wnt protein derived from various organisms can be used. Among these, Wnt protein derived from mammals is preferable. Examples of mammals include humans, mice, rats, cows, pigs and rabbits. Examples of mammalian Wnt protein include Wnt1, Wnt2, Wnt2b, Wnt3, Wnt3a, Wnt4, Wnt5a, Wnt5b, Wnt6, Wnt7a, Wnt7b, Wnt8a, Wnt8b, Wnt9a, Wnt9b, Wnt10a, Wnt10b, Wnt11 and Wnt16. A plurality of types of Wnt protein may be used in combination in the cell culture medium for culturing organoid of the present embodiment.

An example of a method for producing Wnt protein consists of producing Wnt protein using Wnt protein-expressing cells. There are no particular limitations on the origin of the Wnt protein-expressing cells (such as species or culture form) and are only required to be cells that express Wnt protein stably and may be cells that express Wnt protein transiently. Examples of Wnt protein-expressing cells include L dells stably expressing mouse Wnt3a (ATCC CRL-2647) and L cells stably expressing mouse Wnt5a (ATCC CRL-2814). In addition, Wnt protein-expressing cells can also be produced using a known gene recombination technology. Namely, Wnt protein-expressing cells can be produced by inserting DNA encoding a desired Wnt protein into a known expression vector and introducing the resulting expression vector into suitable host cells. The base sequence of the gene that encodes the desired Wnt protein can be acquired from a known database such as GenBank.

The Wnt protein expressed by Wnt protein-expressing cells may be a fragment of Wnt protein and may contain an amino acid sequence other than the amino acid sequence of Wnt protein provided it has Wnt activity. There are no particular limitations of the amino acid sequence other than amino acid sequence of Wnt protein, and an example thereof is the amino acid sequence of an affinity tag. In addition, the amino acid sequence of the Wnt protein is not required to completely coincide with an amino acid sequence acquired from a known database such as GenBank, but rather may be an amino acid sequence that is substantially identical to an amino acid sequence able to be acquired from a known database provided it has Wnt activity.

Examples of amino acid sequences that are substantially identical to an amino acid sequence of Wnt protein able to be acquired from a known database such as GenBank include amino acid sequences in which one to a plurality of amino acids have been deleted, substituted or added.

An "amino acid sequence in which one to a plurality of amino acids have been deleted, substituted or added" refers to an amino acid sequence in which amino acids in roughly a number thereof that can be deleted, substituted or added (preferably 10 or less, more preferably 7 or less and even more preferably 6 or less) have been deleted, substituted or added by a known mutant protein production method such as site-specific mutagenesis.

In addition, examples of substantially identical amino acid sequences include amino acid sequences in which identity with an amino acid sequence able to be acquired from a known database is at least 80% or more, preferably at least 85% or more, more preferably at least 90% or more, even more preferably at least 92% or more, particularly preferably at least 95% or more, and most preferably at least 99% or more.

Wnt protein activity can be confirmed by, for example, TCF reporter assay. In general, a TCF reporter assay refers to a method consisting of introducing a luciferase gene having a binding sequence for T-cell factor (TCF), which is a transcription factor that is specifically activated when a Wnt signal enters a cell and simply evaluating the intensity of Wnt protein activity based on the luminescence of the luciferase (reference document: Molenaar, et al., Cell, 86, 391, 1996). An example of a method other than the TCF reporter assay consists of utilizing the stabilization of β-catenin in a cell when a Wnt signal enters that cell and then quantitatively evaluating the amount of β-catenin by western blotting (reference document: Shibamoto, et al., Gene to cells, 3, 659, 1998). In addition, an example of a method that can be used to evaluate the activity of Wnt protein that imparts a signal to cells via a non-canonical pathway in the manner of Wnt5a consists of evaluating the phosphorylation of an intracellular adapter protein in the form of Dvl2 (reference document: Kikuchi, et al., EMBO J., 29, 3470, 2010).

[R-Spondin]

Examples of a type of Wnt agonist in the form of R-spondin include members of the R-spondin family composed of R-spondin 1, R-spondin 2, R-spondin 3 and R-spondin 4. The R-spondin family consists of secretory proteins that are known to be involved in activation and control of the Wnt signal transduction pathway. A plurality of types of R-spondin may be used in combination in the cell culture medium for culturing organoid of the present embodiment.

The R-spondin may be a fragment of R-spondin or contain an amino acid sequence other than the amino acid sequence of R-spondin provided it has R-spondin activity.

[Content]

The concentration of Wnt protein contained in the cell culture medium for culturing organoid of the present embodiment is preferably 50 ng/mL or more, more preferably 10 ng/mL to 10 μg/mL, even more preferably 200 ng/mL to 1 μg/mL and particularly preferably 300 ng/mL to 1 μg/mL. Wnt agonist is preferably added to the culture medium every two days when culturing epithelial stem cells, and the cell culture medium for culturing organoid is preferably replaced with fresh medium every four days.

[GSK-3β Inhibitor]

Known GSK-3R inhibitors include CHIR-99021, CHIR-98014 (Sigma-Aldrich) lithium (Sigma), kenpaullone (Biomol. International, Leost, M., et al. (2000), Eur. J. Biochem. 287, 5983-5994), 6-bromoindirubin-30-acetoxime (Meyer, L., et al. (2003) Chem. Biol. 10, 1255-1266), SB 218763 and SB 415286 (Sigma-Aldrich) as well as members of the FRAT family and FRAT-derived peptides that inhibit interaction between GSK-3 and axin. An overview thereof is indicated in Meijer, et al. (2004) Trends in Pharmacological Sciences 25, 471-480, which is incorporated in the present description by reference. Methods and assays for determining the level of GSK-3β inhibitor are known among persons with ordinary skill in the art and examples thereof include the method and assay described in Liao, et al. (2004), Endocrinology, 145(6), 2941-2949.

<Afamin>

In the present description, "afamin" refers to a glycoprotein belonging to the albumin family that is known to be present in blood or body fluid. Afamin derived from animals from which the serum is sampled is contained in serum normally added to medium used for cell culturing. Since serum contains impurities and the like other than afamin, afamin is preferably used along without using serum in the cell culture medium for culturing organoid of the present embodiment.

There are no particular limitations on the source of the afamin contained in the cell culture medium for culturing organoid of the present embodiment, and afamin derived from various organisms can be used. Among these, afamin derived from mammals is preferable. Examples of mammals include the same as those in the previously described section entitled, "Wnt Protein". Main amino acid sequences of mammalian afamin along with the base sequences of genes encoding those amino acid sequences can be acquired in a known database such as GenBank. For example, the amino acid sequence of human afamin is registered in GenBank under the accession number AAA21612 and the base sequence of the gene encoding that sequence is registered in under the accession number L32140, the amino acid sequence of bovine afamin is registered under the accession number DAA28569, and the base sequence of the gene encoding that sequence is registered under the accession number GF060968.

The afamin contained in the cell culture medium for culturing organoid of the present embodiment may be purified according to a known method in the case of naturally-occurring afamin contained in serum and the like or may be in the form of recombinant afamin. Recombinant afamin can be produced by suitably using a known gene recombination technology. An example of a method for producing recombinant afamin consists of inserting DNA encoding afamin into a known expression vector, introducing the resulting expression vector into a suitable host cell to express recombinant afamin, and then purifying the recombinant afamin using a known purification method. The recombinant afamin may be afamin to which an affinity tag has been added. There are no particular limitations on the added affinity tag and can be suitably selected for use from among known affinity tags. The affinity tag is preferably an affinity tag recognized by a specific antibody, and examples thereof include FLAG tag, MYC tag, HA tag and V5 tag.

The aforementioned Wnt protein has strong hydrophobicity as a result of a specific serine residue being modified with a fatty acid (palmitoleic acid). Consequently, Wnt protein is widely known to be extremely difficult to purify and store as a result of being susceptible to agglutination and degeneration when in an aqueous solution.

On the other hand, this modification of a specific serine residue by fatty acid is essential for the physiological activity of Wnt protein and has been reported to be involved in bonding with members of the frizzled receptor family.

In addition, in an aqueous solution, there are also findings indicating that Wnt protein bonds with afamin at a 1:1 ratio to form a complex and become soluble while maintaining a high level of physiological activity (Active and water-soluble form of lipidated Wnt protein is maintained by a serum glycoprotein in afamin/α-albumin, Mihara, E., Hirai, H., Yamamoto, H., Tamura-Kawakami, K., Matano, M., Kikuchi, A., Sato, T., Takagi, J., Elife, 2016 Feb. 23; 5).

On the basis of these findings, Wnt-protein-afamin complex may be produced according to a method consisting of culturing cells expressing both Wnt protein and afamin, or Wnt protein-afamin complex may be produced according to a method consisting of co-culturing Wnt protein-expressing cells and afamin-expressing cells. Activity of Wnt protein in the Wnt protein-afamin complex can be evaluated using methods similar to those used for the aforementioned "Wnt protein".

Although there are no particular limitations thereon, the concentration of afamin in the cell culture medium for culturing organoid of the present embodiment is preferably 50 ng/mL to 10 μg/mL, more preferably 100 ng/mL to 1 μg/mL, and even more preferably 300 μg/mL to 1 μg/mL <Insulin-Like Growth Factor 1 (IGF1)>

In general, "insulin-like growth factor 1 (IGF1)" is also referred to as somatomedin C and is a factor that is secreted by stimulation of growth hormone (GH) primarily in the liver. Nearly all cells of the body (and particularly muscle, bone, liver, kidney, nerve, skin and lung cells) are known to be affected by IGF1. In addition to demonstrating an insulin-like effect, IGF1 has functions that regulate cell growth (and particularly, nerve cells) and development as well as cell DNA synthesis.

Although there are no particular limitations thereon, the concentration of IGF1 contained in the cell culture medium for culturing organoid of the present embodiment is preferably 5 ng/mL to 1 μg/mL, more preferably 10 ng/mL to 1 μg/mL, and even more preferably 50 ng/mL to 500 ng/mL. As a result of making the concentration of IGF1 contained in the cell culture medium for culturing organoid of the present embodiment to be within the aforementioned ranges, epithelial stem cells, epithelial cells or epithelial tumor cells derived from mammals, including humans, tissue at least containing any one of these cells, or tissue unable to be cultured in the prior art, can be cultured for a long period of time without substantially containing EGF and p38 inhibitor.

In addition, an organoid can be formed with high efficiency from epithelial stem cells, epithelial cells or epithelial tumor cells derived from mammals, including humans, tissue at least containing any one of these cells, or tissue unable to be cultured in the prior art.

In addition, during culturing of stem cells, IFG1 is preferably added to the culture medium every two days, and the culture medium is preferably replaced with fresh medium every four days.

<Fibroblast Growth Factor 2 (FGF2)>

In general, fibroblast growth factor 2 (FGF2) refers to a basic fibroblast growth factor that has the functions of promoting the growth of vascular endothelial cells and organizing into a tubular structure, or in other words, promoting vascularization by bonding with fibroblast growth factor receptor (FGFR). In addition, human FGF2 is known to have two isoforms consisting of low molecular weight form (LWL) and high molecular weight form (HWL). LWL is mainly present in cytoplasm and acts in the manner of an autocrine, while on the other hand, HWL is present in the cell nucleus and demonstrates activity by an intracrine mechanism that acts within cells.

Although there are no particular limitations thereon, the concentration of FGF2 contained in the cell culture medium for culturing organoid of the present embodiment is preferably 5 ng/mL to 1 μg/mL, more preferably 10 ng/mL to 1 μg/mL, and even more preferably 50 ng/mL to 500 ng/mL. As a result of making the concentration of FGF2 contained in the cell culture medium for culturing organoid of the present embodiment to be within the aforementioned ranges, epithelial stem cells, epithelial cells or epithelial tumor cells derived from mammals, including humans, tissue at least containing any one of these cells, or tissue unable to be cultured in the prior art, can be cultured for a long period of time without substantially containing EGF and p38 inhibitor.

In addition, an organoid can be formed with high efficiency from epithelial stem cells, epithelial cells or epithelial tumor cells derived from mammals, including humans, tissue at least containing any one of these cells, or tissue unable to be cultured in the prior art.

In addition, during culturing of stem cells, FGF2 is preferably added to the culture medium every two days, and the culture medium is preferably replaced with fresh medium every four days.

<Epiregulin (EREG)>

In general, epiregulin (EREG) refers to an EGF-like growth factor that specifically binds with ErbB1 and ErbB4 among receptors (ErbB1 to ErbB4) of the tyrosine kinase (ErbB) family. EREG is known to stimulate growth of keratin-producing cells, liver cells, fibroblasts and vascular endothelial cells. In addition, EREG is mainly expressed in carcinomas of the bladder, lungs, kidneys and colon, placenta and peripheral white blood cells.

Although there are no particular limitations thereon, the concentration of EREG contained in the cell culture medium for culturing organoid of the present embodiment is preferably 5 ng/mL to 1 μg/mL, more preferably 10 ng/mL to 1 μg/mL, and even more preferably 50 ng/mL to 500 ng/mL. As a result of making the concentration of EREG contained in the cell culture medium for culturing organoid of the present embodiment to be within the aforementioned ranges, epithelial stem cells, epithelial cells or epithelial tumor cells derived from mammals, including humans, tissue at least containing any one of these cells, or tissue unable to be cultured in the prior art, can be cultured for a long period of time without substantially containing EGF and p38 inhibitor.

In addition, an organoid can be formed with high efficiency from epithelial stem cells, epithelial cells or epithelial tumor cells derived from mammals, including humans, tissue at least containing any one of these cells, or tissue unable to be cultured in the prior art.

In addition, during culturing of stem cells, EREG is preferably added to the culture medium every two days, and the culture medium is preferably replaced with fresh medium every four days.

<BMP Inhibitor>

Bone morphogenetic protein (BMP) binds as a dimer ligand to a receptor complex consisting of two different types of receptors of serine/threonine kinase, type I and type II receptors. Type II receptor phosphorylates the type I receptor thereby resulting in activation of the receptor kinase. This type I receptor subsequently phosphorylates a specific receptor substrate (SMAD) resulting in induction of transcription activity by a signal transduction pathway. In general, BMP inhibitor prevents or inhibits the formation of complex that neutralizes BMP activity, for example, and is a chemical agent that binds to BMP molecules in order to form a receptor that neutralizes BMP activity. In addition, BMP inhibitor also binds to BMP receptor, for example, to prevent or inhibit binding of BMP molecules to receptors, and is a chemical agent that acts as an antagonist or inverse agonist.

BMP inhibitor has inhibitory activity that is preferably 50% or more, more preferably 70% or more, even more preferably 80% or more and particularly preferably 90% or more than the level of BMP activity in the absence of this inhibitor. BMP inhibitory activity can be evaluated by measuring BMP transcription activity using a method known among persons with ordinary skill in the art (reference document: Zilberberg, et al., BMC Cell Biol., 41, 2007).

A naturally-occurring BMP binding protein is preferable for the BMP inhibitor contained in the cell culture medium for culturing organoid of the present embodiment, and examples thereof include chordin-like proteins such as noggin, gremlin, chordin or chordin domain, follistatin-related proteins such as follistatin or follistatin domain, DAN-like proteins such as DAN or DAN cysteine knot domain, sclerostin/SOST, decorin and α-2 macroglobulin.

Chordin-like protein or DAN-like protein is preferable for the BMP inhibitor contained in the cell culture medium for culturing organoid of the present embodiment and chordin-like protein is more preferable. Noggin is preferable for the chordin-like protein. Chordin-like protein and DAN-like protein are diffusing proteins that are able to inhibit BMP molecules from approaching signal transduction receptors by binding to BMP molecules with various degrees of affinity. In the case of culturing epithelial stem cells, these BMP inhibitors are able to prevent loss of stem cells by adding to cell culture medium for culturing organoid.

The concentration of BMP inhibitor contained in the cell culture medium for culturing organoid of the present embodiment is preferably 10 ng/mL to 100 ng/mL, more preferably 20 ng/mL to 100 ng/mL, and even more preferably 500 ng/mL to 100 ng/mL. During culturing of stem cells, BMP inhibitor is preferably added to the culture medium every two days, and the culture medium is preferably replaced with fresh medium every four days.

<TGF-β Inhibitor>

Transforming growth factor β (TGF-β) is a type of growth factor that is produced in nearly all cells such as those of the kidneys, bone marrow and platelets. There are five subtypes of TGF-β (β1-β5). In addition, TGF-β is known to promote the growth of fibroblasts along with the synthesis and growth of connective tissue in the manner of collagen while also acting suppressively on epithelial cell growth and osteoclasts. In general, TGF-β inhibitor is a chemical agent that prevents or inhibits binding of TGF-β to TGF-β receptors and binds with TGF-β to form a complex that neutralizes TGF-β activity. In addition, TGF-β inhibitor is a chemical agent that prevents or inhibits binding of TGF-β to TGF-β receptors by binding with TGF-β receptors, for example, thereby acting as an agonist or antagonist.

TGF-β inhibitor has inhibitory activity that is preferably 50% or more, more preferably 70% or more, even more preferably 80% or more and particularly preferably 90% or more than the level of TGF-β activity in the absence of this inhibitor. TGF-β activity can be evaluated by a method known among persons with ordinary skill in the art. An example of an evaluation system consists of a cell assay of stably transfected cells using a reporter construct containing human PAI-1 promoter or Smad binding site acting on luciferase reporter gene (reference document: De Gouville, et al., Br. J. Pharmacol., 145(2): 166-177, 2005).

Examples of TGF-β inhibitor contained in the cell culture medium for culturing organoid of the present embodiment include A83-01
(3-(6-methylpyridin-2-yl)-1-phenylthiocarbamoyl-4-quinolin-ylpyrazole), ALK5 inhibitor I
(3-(pyridin-2-yl)-4-(4-quinolyl)-1H-pyrazole), LDN1931189
(4-(6-(4-piperazin-1-yl)phenyl)pyrazolo[1,5-a]pyrimidin-3-yl)quinoline), SB431542
(4-[4-(1,3-benzodioxol-5-yl)-5-pyridin-2-yl-1H-imidazol-2-yl]benzamide), SB-505124
(2-(5-benzo[1,3]dioxol-5-yl-2-tert-butyl-3H-imidazol-4-yl)-6-methylpyridine hydrochloride hydrate), SD-208 (2-(5-chloro-2-fluorophenyl)pteridin-4-yl)pyridin-4-yl-amine), SB-525334
(6-[2-(1,1-dimethylethyl)-5-(6-methyl-2-pyridinyl)-1H-imidazol-4-yl]quinoxaline) LY-364947 (4-[3-(2-pyridinyl)-1H-pyrazol-4-yl]-quinoline), LY2157299
(4-[2-(6-methyl-pyridin-2-yl)-5,6-dihydro-4H-pyrrolo[1,2,-b]pyrazol-3-yl]-quinoline-6-carb oxylic acid amide), TGF-β RI kinase inhibitor II 616452
(2-(3-(6-methylpyridin-2-yl)-1H-pyrazol-4-yl)-1,5-naphthyridine), TGF-β RI kinase inhibitor III 616453
(2-(5-benzo[1,3]dioxol-4-yl-2-tert-butyl-1H-imidazol-4-yl)-6-methylpyridine HCl), TGF-β RI kinase inhibitor IX 616463
(4-((4-((2,6-dimethylpyridin-3-yl)oxy)pyridin-2-yl)amino) benzene sulfonamide), TGF-β RI kinase inhibitor VII 616458
(1-(2-((6,7-dimethoxy-4-quinolyl)oxy)-(4,5-dimethylphenyl)-1-ethanone), TGF-β RI kinase inhibitor VIII 616459
(6-(2-tert-butyl-5-(6-methyl-pyridin-2-yl)-1H-imidazol-4-yl)-quinoxaline), AP12009
(TGF-β2 antisense compound "Trabedersen"), Belagenpumatucel-L (TGF-β2 antisense gene-modified allogenic tumor cell vaccine), CAT-152 (Glaucoma-lerdelimumab (anti-TGF-β2 monoclonal antibody), CAT-192 (Metelimumab (human IgG4 monoclonal antibody that neutralizes TGF-β1), and GC-1008 (anti-TGF-β monoclonal antibody). A83-01 is preferable among the TGF-β inhibitors contained in the cell culture medium for culturing organoid of the present embodiment.

The concentration of TGF-β contained in the cell culture medium for culturing organoid of the present embodiment is preferably 10 nM to 10 μM, more preferably 500 nM to 5 μM and even more preferably 500 nM to 2 μM. During culturing of stem cells, TGF-β inhibitor is preferably added to the culture medium every two days, and the culture medium is preferably replaced with fresh medium every four days.

<Other Components>

The cell culture medium for culturing organoid of the present embodiment may also contain Rho kinase (Rock) inhibitor. Examples thereof include Y-27632 ((R)-(+)-trans-4-(1-aminoethyl)-N-(4-pyridyl)cyclohexane carboxamide dihydrochloride hydrate), fasudil (HA1077) (5-(1,4-diazepan-1-ylsulfonyl)isoquinoline), and H-1152 ((S)-(+)-2-methyl-1-[(4-methyl-5-isoquinolyl)sulfonyl]-hexahydro-1H-1,4-diazepine dihydrochloride). In the case of using Y-27632 as a Rock inhibitor, Y-27632 is preferably added for the first two days of culturing stem cells dispersed in single cells. The concentration of Y-27632 contained in the cell culture medium for culturing organoid of the present embodiment is preferably 10 μM.

Gastrin (or a suitable substitute such as Leu15-gastrin) is further added to the cell culture medium for culturing organoid of the present embodiment. The concentration of gastrin (or suitable substitute thereof) contained in the cell culture medium for culturing organoid of the present embodiment is may be, for example, 1 ng/mL to 10 μg/mL, 1 ng/mL to 1 μg/mL or 5 ng/mL to 100 ng/mL.

The cell culture medium for culturing organoid of the present embodiment may also further contain at least one type of amino acid. Examples of amino acids contained in the cell culture medium for culturing organoid of the present embodiment include L-alanine, L-arginine, L-asparagine, L-aspartic acid, L-cysteine, L-cystine, L-glutamic acid, L-glutamine, L-glycine, L-histidine, L-isoleucine, L-leucine, L-lysine, L-methionine, L-phenylalanine, L-proline, L-serine, L-threonine, L-tryptophan, L-tyrosine, L-valine and combinations thereof. In general, the concentration of L-glutamine contained in the cell culture medium is 0.05 g/L to 1 g/L (and normally, 0.1 g/L to 0.75 g/L). In addition, the concentration of other amino acids contained in the cell culture medium is 0.001 g/L to 1 g/L (and normally, 0.01 g/L to 0.15 g/L). The amino acids may be of a synthetic origin.

The cell culture medium for culturing organoid of the present embodiment may further contain at least one type of vitamin. Examples of vitamins contained in the cell culture medium for culturing organoid of the present embodiment include thiamine (vitamin B1), riboflavin (vitamin B2), niacin (vitamin B3), calcium D-pantothenate (vitamin B5), pyridoxal/pyridoxamine/pyridoxine (vitamin B6), folic acid (vitamin B9), cyanocobalamin (vitamin B12), ascorbic acid (vitamin C), calciferol (vitamin D2), DL-α-tocopherol (vitamin E), biotin (vitamin H) and menadione (vitamin K).

The cell culture medium for culturing organoid of the present embodiment may further also contain at least one type of inorganic salt. The inorganic salt contained in the cell culture medium for culturing organoid of the present embodiment is for assisting in maintaining the osmotic equilibrium of cells as well as assisting in regulating the membrane potential thereof. Specific examples of inorganic salts include salts of calcium, copper, lead, magnesium, potassium, sodium and zinc. Salts are normally be used in the form of chlorides, phosphates, sulfates, nitrates and carbonates. Moreover, specific examples thereof include $CaCl_2$, $CuSO_4\text{-}5H_2O$, $Fe(NO_2)\text{-}9H_2O$, $FeSO_4\text{-}7H_2O$, $MgCl$, $MgSO_4$, $KCl$, $NaHCO_3$, $NaCl$, $Na_2HPO_4$, $Na_2HPO_4\text{—}H_2O$ and $ZnSO_4\text{-}7H_2O$.

The cell culture medium for culturing organoid of the present embodiment may further also contain at least one type of sugar capable of serving as a carbon energy source. Examples of sugars contained in the cell culture medium for culturing organoid of the present embodiment include glucose, galactose, maltose and fructose. Among these, glucose is preferable and D-glucose (dextrose) is particularly preferable for the sugar. The concentration of sugar contained in the cell culture medium for culturing organoid of the present embodiment is preferably 1 g/L to 10 g/L.

The cell culture medium for culturing organoid of the present embodiment may also further contain at least one type of trace element. Examples of trace elements contained in the cell culture medium for culturing organoid of the present embodiment include barium, bromium, cobalt, iodine, manganese, chromium, copper, nickel, selenium, vanadium, titanium, germanium, molybdenum, silicon, iron, fluorine, silver, rubidium, tin, zirconium, cadmium, zinc, aluminum and ions thereof.

The cell culture medium for culturing organoid of the present embodiment may also further contain at least one type of supplementary chemical agent. Examples of such supplementary chemical agents include nutrients or growth factors that have been reported to improve stem cell culturing, such as cholesterol, transferrin, albumin, insulin, progesterone, putrescine, selenite or other factors.

<<Method for Culturing Epithelial Stem Cells, Epithelial Cells, Epithelial Tumor Cells or Tissue Containing these Cells>>

First Embodiment

The culture method according to the first embodiment of the present invention is a method for culturing epithelial stem cells, epithelial cells, epithelial tumor cells or tissue at least containing any one of these cells, provided with: an extracellular matrix preparation step for preparing an extracellular matrix, an adhesion step for adhering epithelial stem cells, epithelial cells, epithelial tumor cells or tissue at least containing any one of these cells onto the extracellular matrix, and an organoid formation step for forming an organoid by adding the aforementioned cell culture medium for culturing organoid and culturing the epithelial stem cells, the epithelial cells, the epithelial tumor cells or tissue at least containing any one of these cells, after the cell adhesion step.

According to the culture method of the present embodiment, epithelial stem cells, epithelial cells or epithelial tumor cells derived from mammals, including humans, tissue at least containing any one of these cells, or tissue unable to be cultured in the prior art, can be cultured for a long period of time. In addition, an organoid can be formed with high efficiency from epithelial stem cells, epithelial cells or epithelial tumor cells derived from mammals, including humans, tissue at least containing any one of these cells, or tissue unable to be cultured in the prior art.

The following provides a detailed explanation of each step in the culture method of the present embodiment.

[Extracellular Matrix Preparation Step]

In general, an "extracellular matrix (ECM)" refers to a supramolecular structure present outside the cells of a living organism. This ECM serves as a scaffold for the growth of epithelial stem cells, epithelial tumor cells or tissue containing these cells.

ECM contains various polysaccharides, water, elastin and glycoproteins. Examples of glycoproteins include collagen, entactin (nidogen), fibronectin and laminin.

An example of a method used to prepare ECM is a method that uses connective tissue cells. More specifically, after having cultured ECM-producing cells such as fibroblasts, these cells are extracted followed by the addition of epithelial stem cells, epithelial cells, epithelial tumor cells or tissue containing these cells to enables the use thereof as scaffold.

Examples of ECM-producing cells include osteoclasts mainly producing collagen and proteoglycan, fibroblasts mainly producing type IV collagen, laminin, interstitial proteoglycan and fibronectin, and colon myofibroblasts mainly producing collagen (type I, type III and type IV), chondroitin sulfate proteoglycans, hyaluronic acid, fibronectin and tenascin C. Alternatively, commercially available ECM may also be used. Examples of commercially available ECM include Extracellular Matrix Protein (Invitrogen), and basement membrane preparations derived from Engelbreth-Holm-Swarm (EHS) mouse sarcoma cells (such as Matrigel® manufactured by BD Biosciences). Synthetic ECM such as ProNectin (Sigma Z378666) may also be used. In addition, mixtures of naturally-occurring ECM and synthetic ECM may be used.

In the case of using ECM to culture stem cells, the long-term survival of stem cells and continued survival of undifferentiated stem cells can be enhanced. In the absence of ECM, stem cell cultures are unable to be cultured over a long period of time and continued survival of undifferentiated stem cells is not observed. Moreover, when ECM is present, organoids can be cultured that are unable to be cultured in the absence of ECM.

ECM usually sinks to the bottom of a dish in which cells are suspended. For example, when ECM coagulates at 37° C., the aforementioned cell culture medium for culturing organoid may be added and used by diffusing in the ECM. Cells present in the medium adhere to the ECM by interacting with integrin, for example, as a result of interacting with the surface structure of the ECM.

ECM may be coated onto a culture vessel and the like. In the case of using fibronectin, the ratio coated onto the culture vessel as ECM is preferably 1 µg/cm$^2$ to 250 µg/cm$^2$, more preferably 1 µg/cm$^2$ to 150 µg/cm$^2$, and even more preferably 8 µg/cm$^2$ to 125 µg/cm$^2$.

[Adhesion Step]

Continuing, epithelial stem cells, epithelial cells, epithelial tumor cells or tissue at least containing any one of these cells are prepared. Examples of epithelial stem cells, epithelial cells, epithelial tumor cells and tissue at least containing any one of these cells used in the culture method of the present embodiment include the same cells and tissue as those in the previously described section entitled, <<Cell Culture Medium for Culturing Organoid>>.

Examples of methods used to prepare epithelial cells from the aforementioned tissue include methods known among persons with ordinary skill in the art. For example, crypts can be isolated by allowing a chelating agent and isolated tissue to stand at a constant temperature. This tissue is then washed followed by detaching the epithelial cell layer from the submucosal layer on a glass slide and slicing into thin sections. Subsequently, the thin sections are allowed to stand at a constant temperature in trypsin or preferably a solution containing at least one of EDTA and EGTA followed by separating the undigested tissue fragments and single cells derived from the crypts using, for example, at least one of filtration and centrifugation. Instead of using trypsin, at least one type of other proteolytic enzyme such as collagen or dispase I may be used. A similar method is used to isolate pancreas or stomach fragments.

Examples of methods for isolating stem cells from epithelial tissue include methods known among persons with ordinary skill in the art. Stem cells express at least one of Lgr5 and Lgr6 on the surface thereof (Lgr5 and Lgr6 belong to a superfamily of large G protein coupled receptors (GPCR)). An example of an isolation method consists of preparing a cell suspension from the epithelial tissue, contacting this cell suspension with a chemical substance that binds with at least one of Lgr5 and Lgr6, separating the chemical substance that binds with at least one of Lgr5 and Lgr6, and isolating stem cells from this binding compound.

Specific examples of chemical substances that bind with at least one of Lgr5 and Lgr6 include antibodies, and more specifically, monoclonal antibodies that specifically recognize at least one of Lgr5 and Lgr6 and bind thereto (such as monoclonal antibodies containing mouse and rat monoclonal antibodies). Use of such antibodies makes it possible to isolate stem cells that express at least one of Lgr5 and Lgr6 using, for example, magnetic beads or by passing through a fluorescence-activated cell sorter.

Epithelial stem cells, epithelial cells, epithelial tumor cells or tissue at least containing any one of these cells that have been isolated according to the aforementioned method are seeded and allowed to stand undisturbed on the cell matrix obtained in the aforementioned preparation step. The seeded cells are able to adhere to ECM by interacting with integrin, for example, as a result of interacting with the surface structure of the ECM.

[Organoid Formation Step]

Continuing, after seeding the cells, the aforementioned cell culture medium for culturing organoid is added before the cells dry followed by culturing the cells. The culture temperature is preferably 30° C. to 40° C. and more preferably at about 37° C. Culture time can be suitably adjusted according to the cells used. An organoid can be formed after roughly 1 to 2 weeks after the start of culturing. In addition, cells that were only able to be maintained and cultured for two to three months in the prior art can be maintained and cultured for a long period of time of 3 months or longer (and preferably about 10 months) in the case of the culture method of the present embodiment. Use of the culture method of the present embodiment makes it possible to maintain differentiation ability and suppress the frequency of tumorigenesis to a low level in the case of culturing the aforementioned stem cells.

In addition, culturing may be carried out under hypoxic condition during the organoid formation step. Culturing under hypoxic condition enables organoids to be formed with high efficiency from epithelial stem cells, epithelial cells or epithelial tumor cells derived from mammals, including humans, tissue at least containing any one of these cells, or tissue unable to be cultured in the prior art.

Hypoxic condition in the present embodiment preferably refer to an oxygen concentration of 0.1% to 15%, more preferably 0.3% to 10%, and even more preferably 0.5% to 5%.

Second Embodiment

The culture method according to a second embodiment of the present invention is a method for culturing epithelial stem cells, epithelial cells, epithelial tumor cells or tissue at least containing any one of these cells; provided with: an extracellular matrix preparation step for preparing an extracellular matrix, an adhesion step for adhering epithelial stem cells, epithelial cells, epithelial tumor cells or tissue at least containing any one of these cells onto the extracellular matrix, and an organoid formation step for forming an organoid by adding the cell culture medium for culturing organoid and culturing the epithelial stem cells, the epithelial cells, the epithelial tumor cells or tissue at least containing any one of these cells under hypoxic condition, after the cell adhesion step; wherein, the cell culture medium for culturing organoid contains at least one type of component selected from the group consisting of Wnt agonist composed of Wnt protein and R-spondin, mitogenic growth factor, bone morphogenetic protein (BMP) inhibitor, transforming growth factor β (TGF-β) inhibitor and p38 inhibitor, and the oxygen concentration is preferably 0.1% to 15%, more preferably 0.3% to 10%, and even more preferably 0.5% to 5%.

According to the culture method of the present embodiment, epithelial stem cells, epithelial cells or epithelial tumor cells derived from mammals, including humans, tissue at least containing any one of these cells, or tissue unable to be cultured in the prior art, can be cultured for a long period of time. In addition, an organoid can be formed with high efficiency from epithelial stem cells, epithelial cells or epithelial tumor cells derived from mammals, including humans, tissue at least containing any one of these cells, or tissue unable to be cultured in the prior art.

Each step of the culture method of the present embodiment is the same as that of the aforementioned first embodiment.

In addition, the cell culture medium for culturing organoid used in the culture method of the present embodiment contains at least one type of component selected from the group consisting of Wnt agonist composed of Wnt protein and R-spondin, mitogenic growth factor, BMP inhibitor, TGF-β inhibitor and p38 inhibitor. In addition, in the culture method of the present embodiment, suitable conditions can be selected from among a plurality of conditions corresponding to the cultured cells or type of tissue by preparing and culturing several types of cell culture media for culturing organoid having different compositions under hypoxic and normoxic conditions (oxygen concentration of about 20%), thereby enabling organoids to be formed with high efficiency.

Examples of Wnt agonist, BMP inhibitor and TGF-β inhibitor include the same as those exemplified in the previously described section entitled, <<Cell Culture Medium for Culturing Organoid>>. In addition, the Wnt agonist used preferably forms a complex with afamin. In the culture method of the present embodiment, the use of a cell culture medium for culturing organoid containing a Wnt agonist composed of a complex of Wnt protein and afamin, and R-spondin makes it possible for form an organoid with high efficiency from epithelial stem cells or epithelial tumor cells derived from mammals, including humans, tissue at least containing any one of these cells, or tissue unable to be cultured in the prior art.

In addition, the following provides an explanation of other constituents contained in the cell culture medium for culturing organoid used in the culture method of the present embodiment.

(Mitogenic Growth Factor)

Examples of mitogenic growth factors contained in the cell culture medium for culturing organoid used in the culture method of the present embodiment include a family of growth factors such as epidermal growth factor (EGF), transforming growth factor-α (TGF-α), brain-derived neurotrophic factor (BDNF) or keratinocyte growth factor (KGF). A plurality of types of these mitogenic growth factors may also be used in combination.

EGF is a potent mitogenic factor for various cultured ectodermal cells and mesodermal cells that has a remarkable effect on differentiation of some fibroblasts into specific cells. EGF precursor is present as a membrane-bound molecule that generates a 53-amino acid peptide that stimulates cells after being cleaved by proteolysis. Among these, EGF is preferable for the mitogenic growth factor contained in the aforementioned cell culture medium for culturing organoid. The concentration of EGF contained in the cell culture medium for culturing organoid of the present embodiment is preferably 5 ng/mL to 500 ng/mL, more preferably 100 g/mL to 400 ng/mL, and even more preferably 50 ng/mL to 200 ng/mL.

In addition, the content of EGF is the same as that of KGF in the case of containing KGF in the aforementioned cell culture medium for culturing organoid. In the case of using a plurality of KGF such as KGF1 and KGF2 (also known as FGF7 and FGF10), the total content of KGF is preferably within the aforementioned ranges. When culturing stem cells, mitogenic growth factor is preferably added to the culture medium every two days and the culture medium is replaced with fresh medium every four days.

(p38 Inhibitor)

In the present description, "p38 inhibitor" refers to an arbitrary inhibitor that directly or indirectly down-regulates p38 signal transduction. In general, p38 inhibitor binds to p38, for example and reduces the activity thereof p38 protein kinase constitutes a portion of the family of mitogen-activated protein kinases (MAPK). MAPK are serine/threonine-specific protein kinases that regulate various cell activities such as gene expression, mitosis, differentiation, growth or cell death/apoptosis by responding to an extracellular stimulus such as stress or inflammatory cytokines. p38 MAPK exists as isoforms α, β, β2, γ and δ. In addition, p38 inhibitor is a chemical agent that binds to at least one p38 isoform, for example, and reduces the activity thereof.

p38 inhibitor has inhibitory activity that is preferably 50% or more, more preferably 70% or more, even more preferably 80% or more and particularly preferably 90% or more in comparison with the level of p38 activity in the absence of this inhibitor. The inhibitory effects of p38 inhibitor can be evaluated using a method known among persons with ordinary skill in the art. Examples of such evaluation systems include a method for detecting a phosphorylation site-specific antibody of Thr180/Tyr182 phosphorylation, biochemical recombinant kinase assay, tumor necrosis factor α (TNF-α) secretion assay, and Discover Rx high-throughput screening platform for p38 inhibition (such as that manufactured by Millipore or Sigma-Aldrich).

Examples of p38 inhibitors contained in the cell culture medium for culturing organoid of the present embodiment include SB-202190
(4-(4-fluorophenyl)-2-(4-hydroxyphenyl)-5-(4-pyridyl)-1H-imidazole), SB-203580
(4-[4-(4-fluorophenyl)-2-[4-(methylsulfinyl)phenyl]-1H-imidazol-5-yl]pyridine, VX-702
(6-(N-carbamoyl-2,6-difluoroanilino)-2-(2,4-difluorophenyl)pyridine-3-carboxyamide), VX-745
(5-=(2,6-dichlorophenyl)-2-[(2,4-difluorophenyl)thio]-6H-pyrimido[1,6-b]pyridazin-6-one), PD-169316 (4-(4-fluorophenyl)-2-(4-nitrophenyl)-5-(4-pyridyl)-1H-imidazole), RO-4402257
(6-(2,4-difluorophenoxy)-2-{[3-hydroxy-1-(2-hydroxyethyl)prpropyl]amino}-8-methylpyrido(2,3-D)pyrimidin-7(8h)-one), and BIRB-796
(1-[5-tert-butyl-2-(4-methylphenyl)pyrazol-3-yl]-3-[4-(2-morpholin-4-ylethoxy)naphthalen-1-yl]urea).

The concentration of p38 inhibitor contained in the aforementioned cell culture medium for culturing organoid is preferably 50 nM to 100 μM, more preferably 100 nM to 50 μM and even more preferably 100 nM to 10 μM. When culturing stem cells, p38 inhibitor is preferably added to the culture medium every two days and the culture medium is replaced with fresh medium every four days.

<<Organoid>>

The organoid according a first embodiment of the present invention is obtained by the previously described culture method.

The organoid of the present embodiment can be used in regenerative medicine, basic medical research on epithelial cells, drug response screening and drug development research using patient-derived epithelial organoids.

<Applications>

In one embodiment thereof, the present invention provides the use of the aforementioned organoid for drug response screening, toxicity assays or regenerative medicine.

In the case of using the aforementioned organoid in drug response screening, the organoid is cultured in, for example, a multi-well plate such as a 96-well plate or 384-well plate. Molecules are then identified that have an effect on the organoid using a molecule library. Examples of molecule libraries include an antibody fragment library, peptide phage display library, peptide library (such as LOPAP® available from Sigma-Aldrich, lipid library (available from BioMol), synthetic compound library (such as LOPAP® available from Sigma-Aldrich) or natural compound library (Specs available from TimTec). Moreover, a gene library may also be used. Examples of gene libraries include a cDNA library, antisense library, and siRNA or other non-coding RNA library. An example of a specific method consists of exposing cells to multiple concentrations of a test chemical agent over a certain period of time followed by evaluating the culture at completion of exposure. In addition, although the organoid of the present embodiment specifically targets epithelial tumor cells, it can also be used to identify chemical agents not targeting organoids composed of normal cells.

Moreover, the organoid of the present embodiment can also be used instead of cell lines such as Caco-2 cells in toxicity assays carried out on new candidate drugs or known or new dietary supplements.

Moreover, the organoid of the present embodiment can be used to culture pathogens such as norovirus for which there are currently no suitable tissue cultures or animal models.

In addition, the organoid of the present embodiment is useful in the field of regenerative medicine in the repair of intestinal epithelium following radiation exposure or surgery, in the repair of intestinal epithelium of patients suffering from inflammatory bowel diseases such as Crohn's disease or ulcerative colitis, or in the repair of intestinal epithelium of patients suffering from short bowel syndrome. Moreover, the organoid of the present embodiment is useful in the repair of intestinal epithelium in patients with genetic diseases of the small intestine or colon. In addition, the organoid of the present embodiment is useful in the field of regenerative medicine, for example, as a graft or portion thereof following pancreatectomy or for the treatment of diabetes such as type I diabetes or type II diabetes.

Although the following provides an explanation of the present invention through examples thereof, the present invention is not limited to the following examples.

EXAMPLES

Example 1

(1) Preparation of Cell Culture Medium for Organoid Culturing

First, human recombinant R-spondin 1 (R&D Systems) was added to a commercially available Advanced DMEM/F-12 medium (Thermo Fisher Scientific) to a final concentration of 1 μg/mL followed by the addition of noggin (Peprotech) to a final concentration 100 ng/mL and A83-01 (Tocris) to a final concentration of 500 nM. Moreover, a medium was prepared in which culture supernatant derived from W-Wnt3a/HEK cultured in serum-containing medium was added to a final concentration of Wnt3a of 300 ng/mL (to be referred to as "WNRA medium").

Moreover, at least one type among Epiregulin (Biolegend) to a final concentration of 500 ng/mL, IGF1 (Biolegend) to a final concentration of 500 ng/mL, or FGF2 (Peprotech) to a final concentration of 50 ng/mL, was added to prepare media in which constituents were combined in the manner indicated below.

WNRA+epiregulin medium
WNRA+IGF1 medium
WNRA+epiregulin+IGF1 medium
WNRA+epiregulin+FGF2 medium
WNRA+IGF1+FGF2 medium In addition, medium serving as a control was also prepared in which EGF (Thermo Fisher Scientific) was added to a final concentration of 50 ng/mL (to be referred to as "WNRA+EGF medium"). In addition, medium serving as a reference example was prepared in which SB202190 (Sigma-Aldrich) was further added to a final concentration of 10 µM (to be referred to as "WNRAS+EGF medium").

(2) Culturing of Epithelial Tumor Cells Derived from Colon Tumor

Figure 2:
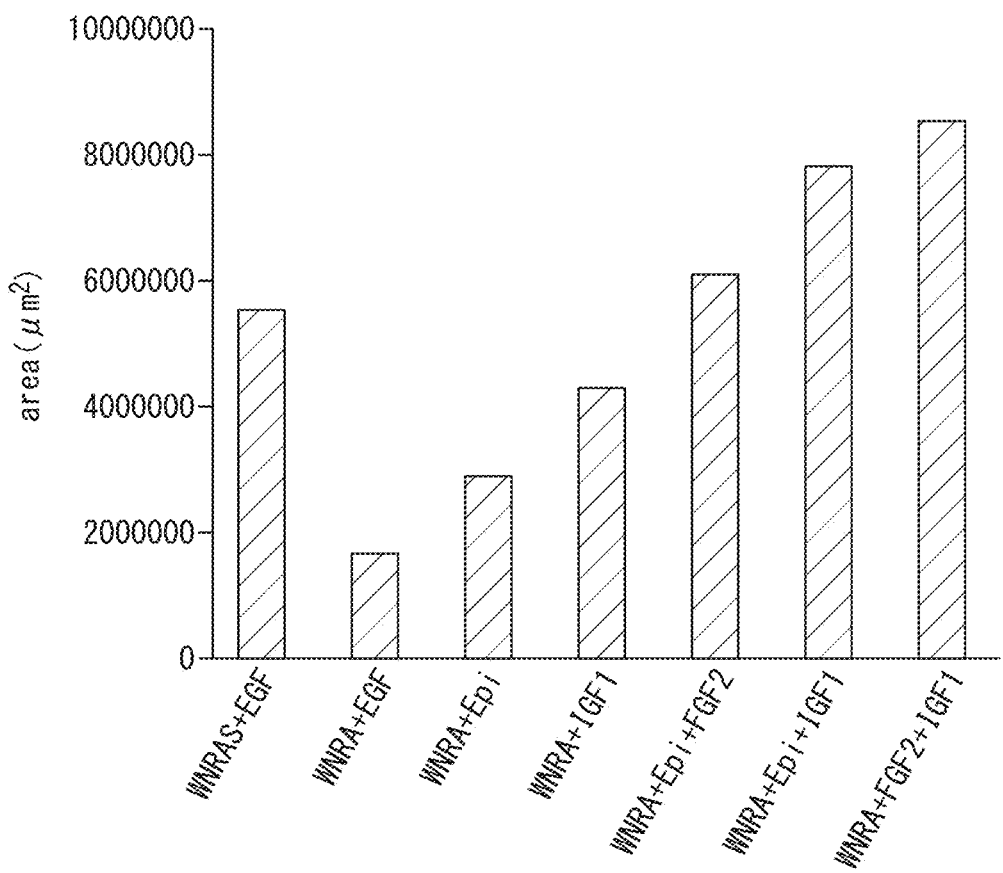
FIG. 2 is a graph quantifying the area in wells occupied by organoids of human epithelial tumor cells on day 7 from the start of primary culturing (passage 0) in each of the media of Example 1. The abbreviations have the same meanings as in FIG. 1.

Lesion tissue from a colon tumor, or a portion at least 5 cm away from the colon tumor treated as normal mucosa, was sampled from colon tumor patients provided with an explanation and from whom consent had been obtained based on an ethics research protocol approved by the ethics committee of Keio University School of Medicine. Next, colon tumor tissue containing epithelial tumor cells derived from human tumor tissue was divided into epithelial tumor cells and residual tissue using Liberase TH. The remaining tissue was further loosely dispersed with trypsin. Next, the epithelial tumor cells were seeded in a 48-well plate together with 25 µL of Matrigel® (BD Bioscience). The WNRA+EGF medium (medium used in conventional methods), WNRA+epiregulin medium, WNRA+IGF1 medium, WNRA+epiregulin+IGF medium, WNRA+epiregulin+FGF2 medium or WNRA+IGF1+FGF2 medium prepared in (1) above were added in aliquots of 250 µL each to the wells seeded with epithelial tumor cells followed by culturing at 37° C. and oxygen concentration of 20%. The medium was replaced every two days from the start of culturing. FIG. 1 shows images depicting the states of the cultures on day 7 from the start of primary culturing (passage 0). FIG. 2 is a graph quantifying the area in the wells occupied by intestinal stem cells for each medium.

Based on FIGS. 1 and 2, organoid area was confirmed to increase and organoids were confirmed to be able to be cultured with high efficiency in comparison with WNRA+EGF medium regardless of the medium used. In particular, organoids were clearly determined to be able to be cultured with high efficiency in the case of using "WNRA+IGF1+FGF2 medium" containing IGF1 and FGF2.

Example 2

(1) Preparation of Cell Culture Medium for Organoid Culturing

First, medium was prepared in which EGF (Thermo Fisher Scientific) to a final concentration of 50 ng/mL, noggin (Peprotech) to a final concentration of 100 ng/mL and A83-01 (Tocris) to a final concentration of 500 nM were added to a commercially available Advanced DMEM/F-12 medium (Thermo Fisher Scientific) (and the resulting medium is also referred to as "ENA medium").

(2) Preparation of Epithelial Tumor Tissue Derived from Colon Tumor

Figure 3:
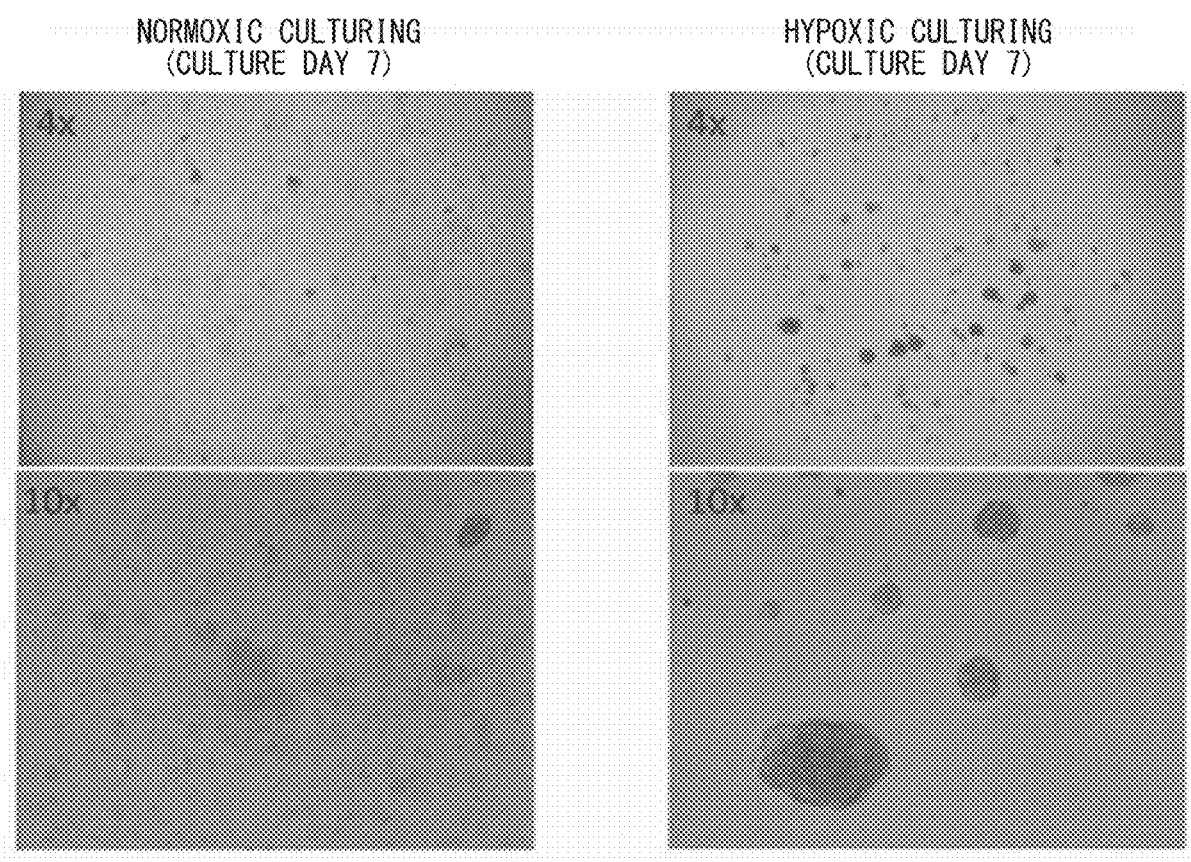
FIG. 3 depicts images indicating cultured organoids of human epithelial tumor cells on day 7 from the start of primary culturing (passage 0) at each oxygen concentration in Example 2.

Epithelial tumor cells were obtained using the methods as those described in sections (1) and (2) of Example 1. Next, the epithelial tumor cells were seeded in a 48-well plate together with 25 µL of Matrigel® (BD Bioscience). 250 µL of the ENA medium prepared in (1) above were added to the wells seeded with epithelial tumor cells followed by culturing at 37° C. and oxygen concentration of 1% (to be referred to as "hypoxic culturing") or oxygen concentration of 20% (to be referred to as "normoxic culturing"). The medium was replaced every two days from the start of culturing. FIG. 3 depicts images indicating cultured organoids on day 7 from the start of primary culturing (passage 0).

Based on FIG. 3, hypoxic culturing condition were confirmed to be essential for forming organoids in the case of the epithelial tumor cells used here.

Figure 4:
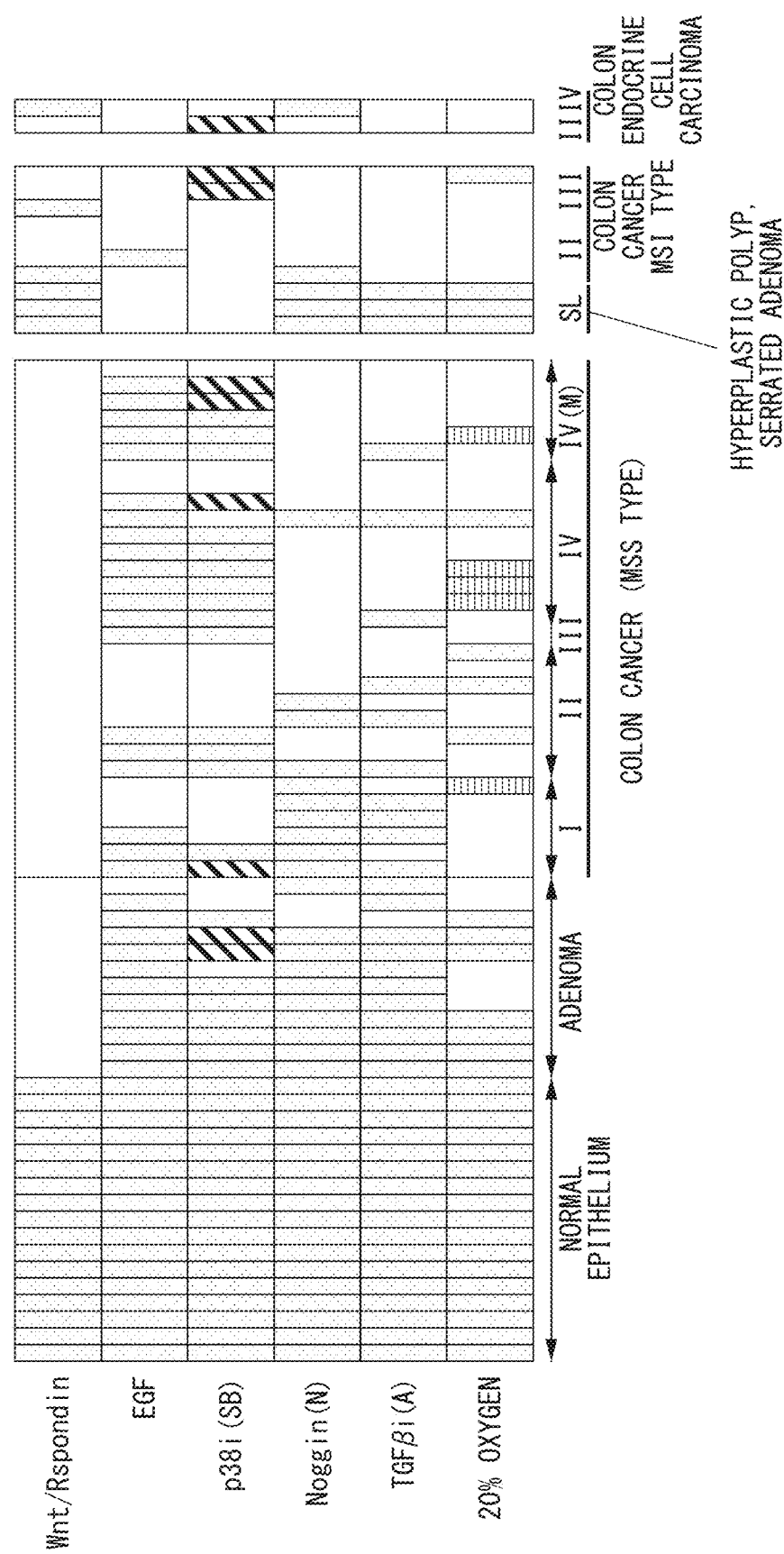
FIG. 4 is a diagram indicating optimal culturing conditions for organoids established from 55 types of colon tumors.

In addition, FIG. 4 is a diagram indicating optimal culturing conditions for organoids established from 55 types of colon tumors. Based on FIG. 4, in the case of culturing normal colon epithelial organoids, in contrast to all constituents consisting of Wnt agonist composed of Wnt protein and R-spondin, EGF, p38 inhibitor, noggin and TGF-β inhibitor being required as constituents contained in the cell culture medium for culturing organoid, in the case of tumor cells, culturing was confirmed to be possible with fewer constituents.

However, there were cases in which a portion of the constituents (and especially p38 inhibitor) exacerbated culturing efficiency accompanying tumorigenesis (refer to the areas containing diagonal lines in FIG. 4). In addition, culturing efficiency worsened under 20% oxygen condition (normoxic condition), while on the other hand, there were cases in which culturing was possible under 1% oxygen condition (hypoxic condition) (refer to the areas containing horizontal lines in FIG. 4). Here, colon cancer IV refers to metastatic colon cancer.

Consequently, all tumors were unable to be cultured under a single set of culturing conditions, and establishment efficiency was clearly determined to improve by preliminarily setting the eight culturing conditions indicated below. In the following culturing conditions, WR(−) indicates that Wnt agonist composed of Wnt protein and R-spondin is not contained, while WR(+) indicates that Wnt agonist composed of Wnt protein and R-spondin is contained.

ENA/WR(−) medium, normoxic culturing
ENA/WR(+) medium, normoxic culturing
ENAS/WR(−) medium, normoxic culturing
ENAS/WR(+) medium, normoxic culturing
ENA/WR(−) medium, hypoxic culturing
ENA/WR(+) medium, hypoxic culturing
ENAS/WR(−) medium, hypoxic culturing
ENAS/WR(+) medium, hypoxic culturing Example 3

(1) Preparation of Wnt3a-Afamin Complex

Wnt3a-afamin complex (to also be referred to as "$W^{Afm}$") was prepared by utilizing the fact that bovine afamin is contained in fetal calf serum, culturing cells introduced only with Wnt3a gene in serum-containing medium, and culturing by utilizing the fact that the secreted Wnt3a automatically forms a stable complex with afamin. In other words, cells expressing Wnt3a having a tag sequence on the N-terminal thereof (W-Wnt3a/HEK) were cultured for 5 days to 7 days in a dish or multilayered flask containing 10& fetal calf serum followed by recovery of the culture supernatant. Continuing, the recovered culture supernatant was subjected to centrifugal separation and passed through a filter (0.22 µm). 220 mL of the collected culture supernatant was used. Continuing, 200 mL of the recovered culture supernatant was added to 3 mL of P20.1 antibody Sepharose, and after mixing by rotating for 3 hours at 4° C., the medium was passed through an empty column to collect the Sepharose. Furthermore, P20.1 antibody is an antibody that specifically recognizes the tag sequence on the N-terminal of Wnt3a. Continuing, the Sepharose that collected in the column was washed with 3 mL of Tris-buffered saline (20 mM Tris-HCl, 150 mM NaCl, pH 7.5) and this washing procedure was repeated five times. Continuing, an eluent was recovered by eluting using 3 mL of peptide solution (0.2 mg/mL PAR4-C8 peptide/TBS) per elution. This elution procedure was repeated ten times to obtain Wnt3a-afamin complex. Wnt3a activity was confirmed by a TCF reported assay using W-Wnt3a/HEK cell supernatant and Wnt3a was confirmed to have a high level of activity in comparison with commercially available Wnt3a (R&D Systems).

(2) Preparation of Cell Culture Medium for Organoid Culturing

First, human recombinant R-spondin 1 (R&D Systems) was added to a commercially available Advanced DMEM/F-12 medium (Thermo Fisher Scientific) to a final concentration of 1 μg/mL followed by the addition of noggin (Peprotech) to a final concentration 100 ng/mL and A83-01 (Tocris) to a final concentration of 500 nM. Moreover, a medium was prepared in which culture supernatant derived from W-Wnt3a/HEK cultured in serum-containing medium was added to a final concentration of Wnt3a of 300 ng/mL, IGF1 (Biolegend) was added to a final concentration of 100 ng/mL, and FGF2 (Peprotech) was added to a final concentration of 50 ng/mL.

In addition, human recombinant R-spondin 1 (R&D Systems) was added to a commercially available Advanced DMEM/F-12 medium (Thermo Fisher Scientific) to a final concentration of 1 μg/mL followed by the addition of noggin (Peprotech) to a final concentration 100 ng/mL and A83-01 (Tocris) to a final concentration of 500 nM. Moreover, medium was prepared in which the Wnt3a-afamin complex prepared in (1) above was added to a final concentration of 300 ng/mL, IGF1 (Biolegend) was added to a final concentration of 100 ng/mL, and FGF2 (Peprotech) was added to a final concentration of 50 ng/mL (and the resulting medium is also referred to as "$W^{Afm}$IFNRA medium").

In addition, human recombinant R-spondin 1 (R&D Systems) was added to a commercially available Advanced DMEM/F-12 medium (Thermo Fisher Scientific) to a final concentration of 1 μg/mL followed by the addition of noggin (Peprotech) to a final concentration 100 ng/mL and A83-01 (Tocris) to a final concentration of 500 nM as Comparative Example 1. Moreover, a medium was prepared in which culture supernatant derived from W-Wnt3a/HEK culture in serum-containing medium was added to a final concentration of Wnt3a of 300 ng/mL, EGF (Thermo Fisher Scientific) was added to a final concentration of 50 ng/mL, and SB202190 (Sigma-Aldrich) was added to a final concentration of 10 μM (and the resulting medium is also referred to as "WENRAS medium").

In addition, human recombinant R-spondin 1 (R&D Systems) was added to a commercially available Advanced DMEM/F-12 medium (Thermo Fisher Scientific) to a final concentration of 1 μg/mL followed by the addition of noggin (Peprotech) to a final concentration 100 ng/mL and A83-01 (Tocris) to a final concentration of 500 nM as Comparative Example 1. Moreover, a medium was prepared in which the Wnt3a-afamin complex prepared in (1) above was added to a final concentration of 300 ng/mL, EGF (Thermo Fisher Scientific) was added to a final concentration of 50 ng/mL, and SBS02190 (Sigma-Aldrich) was added to a final concentration of 10 μM (and the resulting medium may be referred to as "$W^{Afm}$ENRAS medium").

(3) Culturing of Intestinal Stem Cells

A lesion site from a colon tumor, or a portion at least 5 cm away from the colon tumor treated as normal mucosa, was sampled from colon tumor patients provided with an explanation and from whom consent had been obtained based on an ethics research protocol approved by the ethics committee of Keio University School of Medicine. Epithelial cells were extracted from the sampled tissue with EDTA or Liberase TH followed by embedding in Matrigel®.

The Matrigel® containing the epithelial cells (to be referred to as "intestinal stem cells") was seeded into a 48-well plate and cultured together with medium. More specifically, the procedure was as indicated below.

Figure 5A:
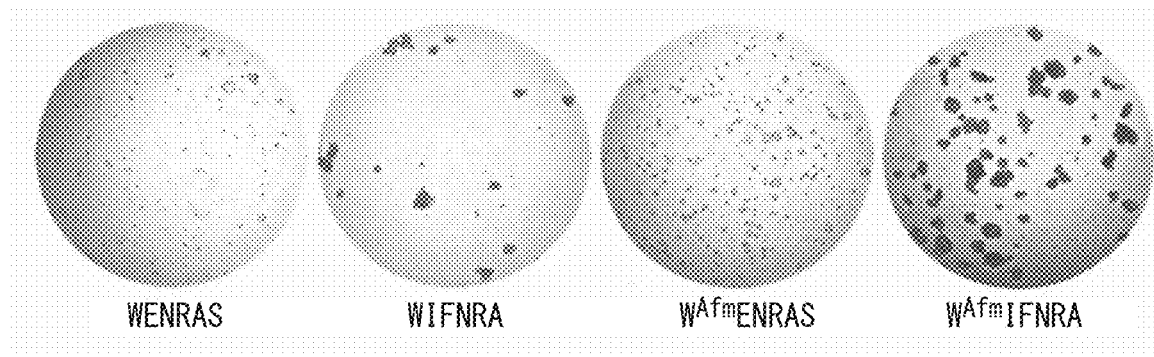
FIG. 5A depicts images of cultured organoids of human intestinal stem cells on day 7 from the start of primary culturing (passage 0) in each of the media of Example 3.
Figure 5B:
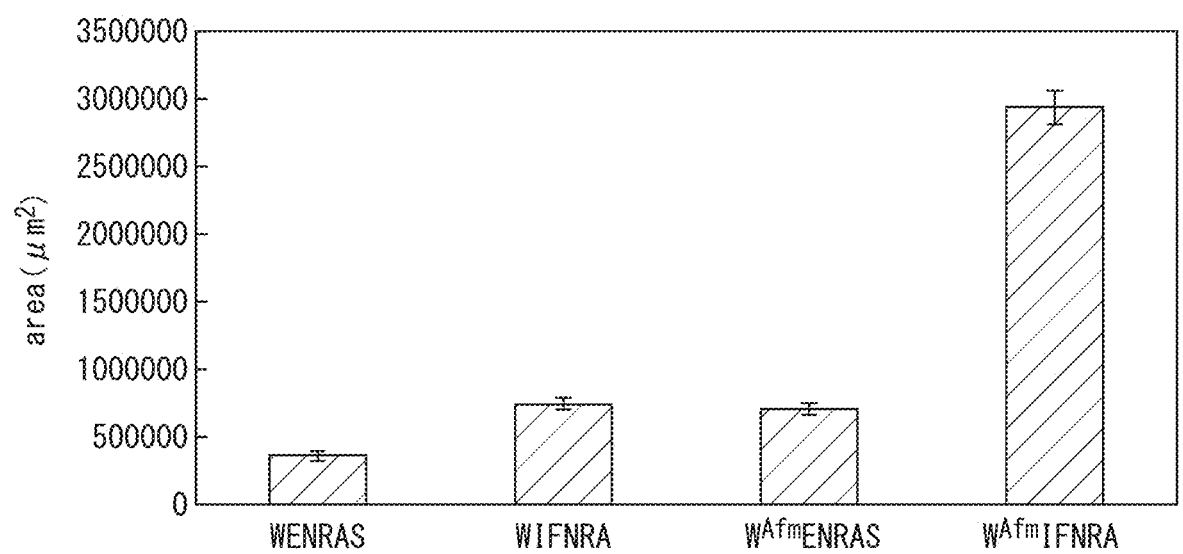
FIG. 5B is a graph quantifying the area in wells occupied by organoids of human intestinal stem cells on day 7 from the start of primary culturing (passage 0) in each of the media of Example 1.

The cultured intestinal stem cells were seeded into a 48-well plate together with 25 μL of Matrigel® (BD Bioscience). 250 μl aliquots of the four types of media prepared in (2) ("WIFRNA medium", "$W^{Afm}$IFNRA medium", "WENRAS medium" and "$W^{Afm}$ENRAS medium") were added to each well followed by culturing at 37° C. and oxygen concentration of 20%. The medium was replaced every two days from the start of culturing. FIG. 5(A) shows images depicting the states of the cultures on day 7 from the start of primary culturing (passage 0), while FIG. 5B is a graph quantifying the area in the wells occupied by organoids of intestinal stem cells in the media. In FIGS. 5(A) and 5(B), "W" indicates Wnt3a containing serum while "$W^{Afm}$" indicates serum-free Wnt3a-afamin complex.

Based on FIGS. 5(A) and 5(B), in the case of using "WENRAS medium" representing conventional culturing condition, the efficiency at which organoids were formed from single intestinal stem cells was poor and the organoids did not grow to an adequate size. On the other hand, in the case of using "WIFRNA" medium, organoids were able to be formed from single intestinal stem cells with better efficiency. Moreover, in the case of substituting conventional serum-containing Wnt3A with serum-free Wnt3a-afamin complex, the culturing efficiency of single normal epithelial cells with IGF1 and IGF2 improved dramatically.

Accordingly, the cell culture medium for culturing organoid of the present embodiment was clearly determined to be extremely effective for improving the efficiency of forming organoids from single cells in applications such as high-throughput screening of normal epithelial cells.

Example 4

(1) Preparation of Wnt3a-Afamin Complex

Wnt3a-afamin complex was prepared using the same method as in section (1) of Example 3.

(2) Preparation of Cell Culture Medium for Organoid Culturing

"WIFNRA medium", "$W^{Afm}$IFNRA medium" and "WENRAS" medium were prepared using the same method as in section (2) of Example 4. In addition, recombinant human R-spondin 1 (R&D Systems) was added to commercially available Advanced DMEM/F-12 medium (Thermo Fisher Scientific) to a final concentration of 1 μg/mL followed by the addition noggin (Peprotech) to a final concentration of 100 ng/mL and A83-01 (Tocris) to a final concentration of 500 nM. Moreover, a medium was prepared in which the Wnt3a-afamin complex prepared in (1) above was added to a final concentration 300 ng/mL, IGF1 (Biolegend) was added to a final concentration of 100 ng/mL, FGF2 (Peprotech) was added to a final concentration of 50 ng/mL, and SBS02190 (Sigma-Aldrich) was added to a final concentration of 10 μM (and the resulting medium may be referred to as "W$^{Afm}$IFNRAS medium").

(3) Culturing of Epithelial Tumor Cells Derived from Colon Tumor

Figure 6:
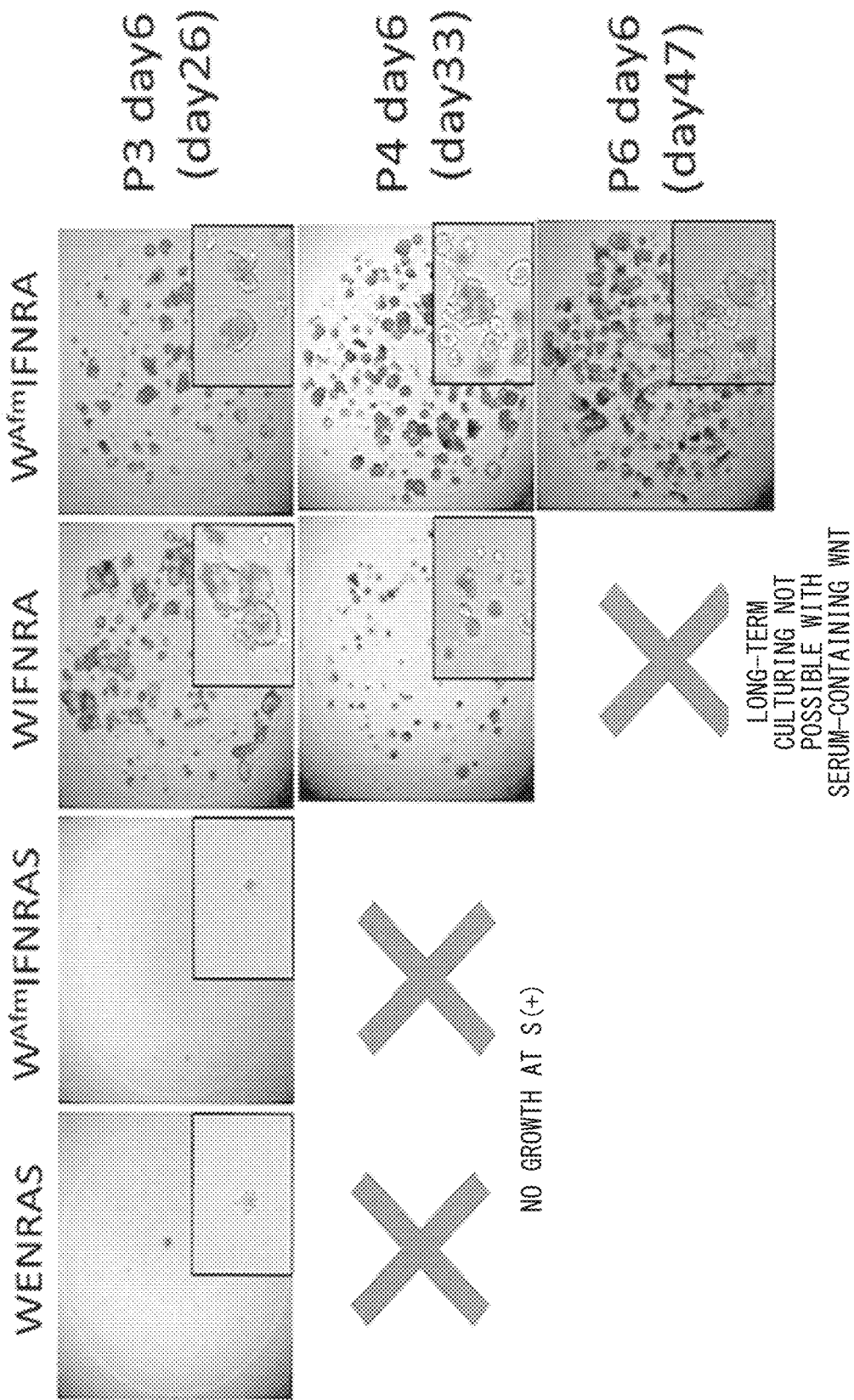
FIG. 6 depicts images indicating organoids of human epithelial tumor cells six days after a third round of subculturing (passage 3) (total number of days cultured: 26), six days after the start of a fourth round of subculturing (passage 4) (total number of days cultured: 33), and six days after the start of a sixth round of subculturing (passage 6) (total number of days cultured; 47).

Epithelial tumor cells were obtained using the same method as in section (2) of Example 1. Next, the epithelial tumor cells were seeded in a 48-well plate together with 25 μL of Matrigel® (BD Bioscience). The "WIFNRA medium", "W$^{Afm}$IFNRA medium", "WENRAS medium" and "WAfmIFNRAS medium" prepared in (2) above were added in 250 μL aliquots to the wells seeded with epithelial tumor cells followed by culturing at 37° C. and oxygen concentration of 20%. The medium was replaced every two days from the start of culturing. FIG. 6 depicts images indicating the states of the cultures six days after the start of the third round of subculturing (Passage 3) (total number of days cultured after start of culturing: 26), six days after the start of the fourth round of subculturing (Passage 4) (total number of days cultured after start of culturing: 33), and six days after the start of the sixth round of subculturing (Passage 6) (total number of days cultured after start of culturing: 47). In FIG. 6, "W" indicates Wnt3a containing serum while "W$^{Afm}$" indicates serum-free Wnt3a-afamin complex.

Based on FIG. 6, the epithelia tumor cells derived from colon tumor used here exhibited toxicity to p38 inhibitor in the form of SB202190 and did not grow in the presence of SBS202190 ("WENRAS medium" and "W$^{Afm}$IFNRAS medium"). On the other hand, organoid formation by epithelial tumor cells was observed as a result of culturing with medium containing IGF1 and FGF2 ("WIFNRA medium").

Moreover, Wnt agonist consisting of Wnt protein and R-spondin was essential for the epithelial tumor cells derived from colon tumor used here, and during culturing with medium containing Wnt3a ("WIFNRA medium"), growth was observed to be inhibited by serum contained in Wnt3a and long-term culturing was not possible. On the other hand, long-term culturing was possible in the case of culturing with medium containing serum-free Wnt3a-afamin complex ("W$^{Afm}$IFNRA medium").

In addition, FIG. 7 is a table indicating the results of evaluating organoid formation efficiency and the possibility of long-term culturing in different compositions of the cell culture medium for culturing organoid of the present embodiment. In FIG. 7, ○ indicates that organoids can be formed and that long-term culturing is possible for about one month, ⊚ indicates that organoids can be cultured efficiently and that long-term culturing is possible for about month, and ⊚⊚ indicates that organoids can be formed even more efficiently and that long-term culturing is possible for about three months. In addition, in FIG. 7, "Normoxia" refers to normoxic culturing condition at an oxygen concentration of about 20%, while "Hypoxia" refers to hypoxic culturing condition at an oxygen concentration of about 1%.

Based on FIG. 7, according to the cell culture medium for culturing organoid or culture method of the present embodiment, organoids were shown to be able to be formed and long-term culturing was shown to be possible, regardless of the cells or tissue, with respect to epithelial stem cells or epithelial tumor cells derived from mammals, including humans, tissue containing at least any one of these cells, or tissue unable to be cultured in the prior art.

According to the cell culture medium for culturing organoid of the present embodiment, epithelial stem cells, epithelial cells or epithelial tumor cells derived from mammals, including humans, tissue at least containing any one of these cells, or tissue unable to be cultured in the prior art, can be cultured for a long period of time.

In addition, an organoid can be formed with high efficiency from at least any one of the aforementioned cells and aforementioned tissue.

In addition, the differentiation ability of epithelial stem cells cultured using the cell culture medium for culturing organoid of the present embodiment can be maintained over a long period of time and the tumor incidence thereof is extremely low.

Moreover, an organoid obtained by the culture method of the present embodiment can be used in regenerative medicine, basic medical research on epithelial cells, drug response screening and drug development research using patient-derived epithelial organoids.

The invention claimed is:
1. A cell culture medium for culturing organoid comprising at least two components selected from the group consisting of:
  insulin-like growth factor 1 (IGF1),
  fibroblast growth factor 2 (FGF2) and
  epiregulin (EREG),
  and further comprising at least one component selected from the group consisting of the following components i) to iii):
  i) Wnt agonist,
  ii) bone morphogenetic protein (BMP) inhibitor, and
  iii) transforming growth factor-β (TGF-β) inhibitor,
  wherein the cell culture medium does not substantially contain EGF and p38 inhibitor.
2. The cell culture medium for culturing organoid according to claim 1, which contains IGF1 and FGF2.
3. The cell culture medium for culturing organoid according to claim 1, wherein the Wnt agonist is selected from the group consisting of Wnt protein, R-spondin and GSK-β inhibitor.
4. The cell culture medium for culturing organoid according to claim 3, wherein the cell culture medium further comprises afamin and the Wnt protein forms a complex with the afamin, which stabilizes the Wnt protein.
5. The cell culture medium for culturing organoid according to claim 3, wherein the Wnt agonist is Wnt protein and R-spondin.
6. The cell culture medium for culturing organoid according to claim 3, wherein the Wnt protein is selected from the group consisting of Wnt1, Wnt2, Wnt2b, Wnt3, Wnt3a, Wnt4, Wnt5a, Wnt5b, Wnt6, Wnt7a, Wnt7b, Wnt8a, Wnt8b, Wnt9a, Wnt9b, Wnt10a, Wnt10b, Wnt11 and Wnt16.
7. The cell culture medium for culturing organoid according to claim 3, wherein the R-spondin is selected from the group consisting of R-spondin 1, R-spondin 2, R-spondin 3 and R-spondin 4.
8. The cell culture medium for culturing organoid according to claim 1, wherein the BMP inhibitor is selected from the group consisting of noggin, gremlin, chordin, chordin-like protein containing a chordin domain, follistatin, follistatin-related protein containing a follistatin domain, DAN, DAN-like protein containing a DAN cysteine knot domain, sclerostin/SOST and α-2 macroglobulin.
9. The cell culture medium for culturing organoid according to claim 8, wherein the BMP inhibitor is noggin.
10. The cell culture medium for culturing organoid according to claim 1, wherein the TGF-β inhibitor is selected from the group consisting of A83-01, SB-431542, SB-505124, SB-525334, SD-208, LY-36494 and SJN-2511.

11. The cell culture medium for culturing organoid according to claim 10, wherein the TGF-β inhibitor is A83-01.

12. The cell culture medium for culturing organoid according to claim 1, which is a serum-free medium.

* * * * *